US009990712B2

(12) United States Patent
Gazit

(10) Patent No.: US 9,990,712 B2
(45) Date of Patent: Jun. 5, 2018

(54) ORGAN DETECTION AND SEGMENTATION

(71) Applicant: Algotec Systems Ltd., Rochester, NY (US)

(72) Inventor: Tiferet Gazit, Tel-Aviv (IL)

(73) Assignee: Algotec Systems Ltd., Ra'anana (IL)

( * ) Notice: Subject to any disclaimer, the term of this patent is extended or adjusted under 35 U.S.C. 154(b) by 106 days.

(21) Appl. No.: 15/086,278

(22) Filed: Mar. 31, 2016

(65) Prior Publication Data

US 2016/0300343 A1 Oct. 13, 2016

Related U.S. Application Data

(60) Provisional application No. 62/144,552, filed on Apr. 8, 2015, provisional application No. 62/217,987, filed on Sep. 14, 2015.

(51) Int. Cl.
*G06K 9/00* (2006.01)
*G06T 7/00* (2017.01)
*A61B 6/03* (2006.01)
*G06T 5/00* (2006.01)
*G06T 7/11* (2017.01)
(Continued)

(52) U.S. Cl.
CPC ............ *G06T 7/0012* (2013.01); *A61B 6/032* (2013.01); *A61B 6/5211* (2013.01); *G06T 5/002* (2013.01); *G06T 5/009* (2013.01); *G06T 7/0014* (2013.01); *G06T 7/11* (2017.01); *G06T 7/187* (2017.01); *A61B 6/481* (2013.01); *A61B 6/482* (2013.01); *G06T 2207/10081* (2013.01); *G06T 2207/20004* (2013.01); *G06T 2207/20081* (2013.01); *G06T 2207/20182* (2013.01); *G06T 2207/20208* (2013.01); *G06T 2207/30084* (2013.01)

(58) Field of Classification Search
CPC ....... G06T 5/002; G06T 5/009; G06T 7/0014; G06T 7/11; G06T 7/187; G06T 7/0012; G06T 2207/10081; G06T 2207/20004; G06T 2207/20081; G06T 2207/20182; G06T 2207/20208; G06T 2207/30084; A61B 6/032; A61B 6/5211; A61B 6/481; A61B 6/482
See application file for complete search history.

(56) References Cited

U.S. PATENT DOCUMENTS 7,260,249 B2 8/2007 Smith
7,623,709 B2 11/2009 Gering
(Continued)

OTHER PUBLICATIONS

Bhattacharyya distance—https://en.wikipedia.org/wiki/Bhattacharyya_distance, 2015, 4 pages.
(Continued)

*Primary Examiner* — Shefali Goradia

(57) ABSTRACT

A method of segmenting a target organ of the body in medical images, the method comprising: providing a probabilistic atlas with probabilities for a presence of the target organ at different locations relative to a bounding region of the target organ; providing one or more medical test images; for each test image, identifying, at least provisionally, a location of a bounding region for the target organ in the test image; and for each test image, using the probabilities from the probabilistic atlas to segment the target organ in the test image, with the segmenting performed by a data processor.

19 Claims, 13 Drawing Sheets

(51) Int. Cl.
*G06T 7/187* (2017.01)
*A61B 6/00* (2006.01)

(56) References Cited

U.S. PATENT DOCUMENTS

| | | | |
|---|---|---|---|
| 7,792,348 B2 | 9/2010 | Russakoff | |
| 7,912,288 B2* | 3/2011 | Winn | G06K 9/342 |
| | | | 382/173 |
| 8,131,038 B2 | 3/2012 | Saddi et al. | |
| 8,170,306 B2 | 5/2012 | Yu et al. | |
| 8,577,115 B2 | 11/2013 | Gering et al. | |
| 8,600,130 B2 | 12/2013 | Järliden | |
| 8,831,312 B2 | 9/2014 | Wang et al. | |
| 9,092,691 B1* | 7/2015 | Beaumont | G06T 7/0014 |
| 9,679,389 B2* | 6/2017 | Ostrovsky-Berman | G06T 7/11 |
| 2010/0007665 A1* | 1/2010 | Smith | G06T 13/40 |
| | | | 345/473 |
| 2012/0236995 A1 | 9/2012 | Eusemann et al. | |
| 2013/0274589 A1 | 10/2013 | Gross et al. | |
| 2014/0005538 A1 | 1/2014 | Florent et al. | |
| 2015/0287188 A1 | 10/2015 | Gazit et al. | |
| 2016/0300351 A1 | 10/2016 | Gazit | |

OTHER PUBLICATIONS

Active contour model—https://en.wikipedia.org/wiki/Active_contour_model, 2015, 9 pages.

Commonly Assigned U.S Appl. No. 61/974,077, filed Apr. 2, 2014 entitled "Organ-Specific Image Display," by Reuven R. Shreiber et al.

Xiangrong Zhou et al., "Automatic organ segmentation on torso CT images by using content-based image retrieval," Proc. of SPIE, 2012, vol. 8314, pp. 83143E-1-83143E-8.

A. Criminisi et al., "Regression forests for efficient anatomy detection and localization in computed tomography scans," Medical Image Analysis, 17 (2013), pp. 1293-1303.

Xiangrong Zhou et al., "Automatic localization of solid organs on 3D CT images by a collaborative majority voting decision based on ensemble learning," Computerized Medical Imaging and Graphics, 36 (2012), pp. 304-313.

Hyunjin Park et al., "Construction of an Abdominal Probabilistic Atlas and its Application in Segmentation," IEEE Transactions on Medical Imaging, vol. 22, No. 4, Apr. 2003, pp. 483-492.

Chien-Cheng Lee et al., "Identifying Multiple Abdominal Organs From CT Image Series Using a Multimodule Contextual Neural Network and Spatial Fuzzy Rules," IEEE Transactions on Information Technology in Biomedicine, vol. 7, No. 3, Sep. 2003, pp. 208-217.

J.A. Sethian, Level Set Methods and Fast Marching Methods: Evolving Interfaces in Computational Geometry, Fluid Mechanics, Computer Vision, and Materials Science (Cambridge University Press, 1996).

Commonly Assigned U.S. Appl. No. 62/217,987, filed Sep. 14, 2015 entitled "Image Processing of Organs Depending on Organ Intensity Charateristics," by Tiferet Gazit.

* cited by examiner

ORGAN DETECTION AND SEGMENTATION

CROSS REFERENCE TO RELATED APPLICATION

This application claims the benefit of: (1) U.S. Provisional application U.S. Ser. No. 62/144,552, provisionally filed on Apr. 8, 2015, entitled ORGAN DETECTION AND SEGMENTATION, in the name of Tiferet T. Gazit, which is incorporated herein by reference in entirety, and (2) U.S. Provisional application U.S. Ser. No. 62/217,987 provisionally filed on Sep. 14, 2015, entitled IMAGE PROCESSING OF ORGANS DEPENDING ON ORGAN INTENSITY CHARACTERISTICS, in the name of Tiferet T. Gazit, which is incorporated herein by reference in entirety.

FIELD AND BACKGROUND OF THE INVENTION

The present invention, in some embodiments thereof, relates to segmenting an organ or other structure in a medical image and, more particularly, but not exclusively, to automatically detecting and segmenting a target organ.

Segmentation digital medical images, identifying organs and other structures, has traditionally been done manually by human experts, or semi-automatically, with human experts interacting with, and providing critical input to, segmentation software running on a computer. It is desirable to find fully automatic methods of segmenting medical images, without the need for labor-intensive input from human experts.

Zhou et al, "Automatic organ segmentation on torso CT images by using content-based image retrieval," in Medical Imaging 2012: Image Processing, edited by David R. Haynor and Sebastien Ourselin, Proc. of SPIE Vol. 8314, describes "atlas-based organ segmentation techniques" which aims "to generate an atlas that predicts the prior probability [that] each voxel in the inputted CT case belongs to the target organ region. This prior probability is calculated from a number of additional CT cases that are pre-stored in a database." The atlas is generated specifically for the input CT image that is being segmented (referred to as the "query image"), and "the proposed scheme searches all the CT images in [the] database and selects a number of CT cases that have similar organ appearances to the query images, since "the appearances of the organ regions for query images and the CT images for atlas construction should be similar. The atlas p shows the prior probability of the organ existence on each voxel within the bounding box of the input image." In order to construct the atlas, each of the CT images in the database is registered with the query image by finding "the value of the cross correlation function between the two images and maximiz[ing] this value to accomplish the spatial registration (rigid deformation) of the two images," and only the database images which have the highest cross-correlation function with the query image are selected for the atlas.

U.S. Pat. No. 8,600,130 (Jarliden) describes a means for receiving a three-dimensional representation of a patient, a computing means adapted to segment the representation into a region within an anatomic structure and region outside the structure, on the basis of the degree of similarity of voxels to neighboring voxels in the representation, and a dataset representing an a priori assumption of the correct segmentation." The dataset is a probabilistic "atlas [which] is first registered to the current image using (for example) an affine registration technique. Thus the atlas only has to account for the variability after registration." The segmentation "minimizes C," which is "a cost function [that] describes two goals: that each value [of being inside or outside the anatomic structure] should be close to its similar neighbors and that each value should be close to the atlas value." The patent states that, "With the atlas, the technique can become fully automatic, although the user can still—if needed—semi-automatically correct the result." To make the corrections, "the user annotates the image with two types of scribbles, that mark the scribbled pixels as either 'inside' or 'outside'." The patent further states that, "The ability to easily correct the result is probably the most important advantage of this technique."

U.S. Pat. No. 8,577,115 (Gering) describes a "method [that] comprises acquiring an image of [a] patient segmenting the image to categorize at least some image elements according to their substance, [and] aligning [the] segmented image with a probabilistic atlas. A spatially varying prior (SVP) expresses the probability of each tissue class occurring at a given spatial location. The SVP is one component of the statistical probabilistic atlas used for segmentation within this framework. Before the SVP, or any atlas component, can be applied, it must first be registered to the CT scan to be analyzed. Thus, the segmentation module registers the atlas to the CT image by matching bone profiles. The translation in the left-right direction and the scale in the left-right direction can be computed from the bounding box of the body ROI."

U.S. Pat. No. 8,131,038 (Saddi) describes "automatically segmenting a liver in digital medical images," using "a set of training shapes for a liver trained from a set of manually segmented images," and finding "a mean shape [and] eigenmodes" of shape variation.

U.S. Pat. No. 7,792,348 (Russakoff) describes "an image processing unit for using a probabilistic atlas and/or a shape model for cancer detection in mammography images" that "may consist of a baseline breast atlas shape and a set of deformation modes."

U.S. Pat. No. 7,623,709 (Gering) describes "fitting a topological atlas to acquired image data and generating spatially varying priors. The method further includes segmenting the acquired image data based on the spatially varying priors. The topological atlas comprises a plurality of structures, wherein each structure corresponds to a simple shape such as a circle, an ellipse, a hyperbola, and triangle. The topological atlas approximates the shape of the anatomical region captured in the image data."

U.S. Pat. No. 8,831,312 (Wang) describes a method of "left ventricle and myocardium segmentation," in MRI images of the heart. "A cost is computed by combining the normalized intensity difference and gradient."

The Wikipedia article on "Active contour model," downloaded from <http://en.wikipedia.org/wiki/Active_contour_model> on Nov. 30, 2014, describes "an active contour model, also called snakes, [as] a framework for delineating an object outline from a 2D image. The framework attempts to minimize an energy associated to the contour as a sum of an internal and external energy. The external energy is supposed to be minimal when the snake is at the object boundary position, [for example] giving low values when the regularized gradient around the contour position reaches its peak value. The internal energy is supposed to be minimal when the snake has a shape which is supposed to be relevant considering the shape of the sought object. The most straightforward approach grants high energy to elongated contours (elastic force) and to bended/high curvature contours (rigid force), considering the shape should be as regular and smooth as possible".

Additional background is described in U.S. Pat. No. 8,170,306 (Yu), U.S. Pat. No. 7,260,249 (Smith), U.S. 2012/0236995 (Eusemann), U.S. 2013/0274589 (Gross), and U.S. 2014/0005538 (Florent).

SUMMARY OF THE INVENTION

An aspect of some embodiments of the invention concerns using a probabilistic atlas showing the location of a target organ in a bounding region of the organ, for example a rectangular box oriented along the principle body directions, in order to segment the target organ in one or more test images.

There is thus provided, in accordance with an exemplary embodiment of the invention, a method of segmenting a target organ of the body in medical images, the method comprising: a) providing a probabilistic atlas with probabilities for a presence of the target organ at different locations relative to a bounding region of the target organ; b) providing one or more medical test images; c) for each test image, identifying, at least provisionally, a location of a bounding region for the target organ in the test image; and d) for each test image, using the probabilities from the probabilistic atlas to generate a segmentation mask the target organ in the test image, with the generating performed by a data processor.

Optionally, the method also comprises displaying, storing, or transmitting the generated segmentation mask, or information obtained from the generated segmentation mask. Optionally, the method also comprises generating the probabilistic atlas. Optionally, generating the probabilistic atlas is done independently of the test image. Optionally, generating the probabilistic atlas is done before providing the test image. Optionally, the method also comprises selecting a set of training images of the target organ to use in generating the probabilistic atlas, independently of the test image, and generating the probabilistic atlas is done using all of the selected training images. Optionally, selecting the set of training images is done before providing the test image. Optionally, the probabilistic atlas has a gradient in probability as a function of location, that is greatest within one voxel of a location corresponding to a boundary of the bounding region. Optionally, the probabilistic atlas has a gradient in probability as a function of location, that is greatest at a location where the probability is less than 0.2. Optionally, at least 15% of the voxels in the atlas corresponding to locations in the bounding region have probability between 20% and 80%.

Optionally, the bounding region can be completely parameterized by upper and lower bounds in each of three principal body directions, and using the probabilities from the probabilistic atlas to generate the segmentation mask of the target organ comprises: a) registering the bounding region of the target organ identified in the test image to the probabilistic atlas, by matching the upper and lower bounds in each of the three body directions to upper and lower bounds of the probabilistic atlas in each of the three body directions; and b) using the probabilistic atlas to find a probability for each voxel in the bounding region in the test image to belong to the target organ, according to the registration.

Optionally, using the probabilities from the probabilistic atlas to generate the segmentation mask of the target organ comprises: a) finding a weighting factor for each voxel in the bounding region identified in the test image, based on the probabilistic atlas; b) calculating information on a weighted distribution of intensities, for the voxels in the bounding region of the test image, each voxel weighted by the weighting factor; and c) using the information on the weighted distribution of intensities to generate the segmentation mask of the target organ.

Optionally, using the information on the weighted distribution of intensities comprises using the information to find one or more parameters of contrast agent use in the test image. Optionally, using the information on the weighted distribution of intensities comprises finding a core region of voxels that have locations within the bounding region where the target organ is likely to be located according to the probabilistic atlas, and most of which have intensity values expected for the target organ according to the information on the weighted distribution of intensities.

Optionally, using the information on the weighted distribution of intensities comprises: a) selecting one or more seed voxels for the target organ in the bounding region; and b) using a region-growing algorithm to generate the segmentation mask of the target organ starting from the one or more seed voxels, the region-growing algorithm using a cost function whose value at each voxel depends on a value or values of the weighted distribution of intensities at or close to the voxel's intensity.

Optionally, generating the segmentation mask of the target organ comprises finding a core region of voxels that have locations within the bounding region where the target organ is considered likely to be located according to the probabilistic atlas, and most of which have intensity values expected for the target organ.

Optionally, the method also comprises estimating values of one or more parameters of contrast agent use in the test image from information on an intensity distribution of voxels in the bounding region, wherein finding the core region comprises finding voxels that match intensity values expected for those values of parameters of contrast agent use.

In an exemplary embodiment of the invention, using the probabilities of the probabilistic atlas to generate the segmentation mask of the target organ in the test image comprises: a) using the probabilistic atlas to find one or more voxels in the test image that are considered likely to belong to the target organ; and b) using a region-growing algorithm to generate the segmentation mask of the target organ starting from the one or more voxels as seed voxels.

Optionally, the one or more voxels are considered likely to belong to the target organ because of a combination of the voxels corresponding to locations in the probabilistic atlas with high probabilities, and the voxels having intensities expected for the target organ according to an analysis of a set of training images of the target organ. Optionally, the one or more voxels correspond to locations in the probabilistic atlas with the maximum probability of any locations in the probabilistic atlas.

In an exemplary embodiment of the invention, using the probabilities of the probabilistic atlas to generate the segmentation mask of the target organ in the test image comprises using a region-growing algorithm to generate the segmentation mask of the target organ starting from one or more seed voxels, the region-growing algorithm using a cost function that depends on probability values of voxels being located in the target organ according to the probabilistic atlas.

Optionally, the one or more seed voxels have locations within the bounding region where the target organ is considered likely to be located according to the probabilistic atlas.

Optionally, using the probabilities of the probabilistic atlas to generate the segmentation mask of the target organ also comprises finding a core region of voxels that have locations within the bounding region where the target organ is likely to be located according to the probabilistic atlas, and most of which have intensity values expected for the target organ.

Optionally, the one or more seed voxels are located in the core region, and the region-growing algorithm is programmed to stop the growing at any voxel for which a path cost exceeds a threshold cost, and the cost function of most voxels in the core region is sufficiently low so that the path cost of most voxels in the core region is less than 20% of the threshold cost.

Optionally, the method also comprises: a) using the segmentation mask of the target organ to find a second estimate of a location of the bounding region in the image; and b) using the probabilistic atlas and the second estimate of the location of the bounding region to find a second segmentation mask of the target organ.

There is further provided, according to an exemplary embodiment of the invention, a system for segmenting a target organ in a medical image, the system comprising: a) an input device that receives a digital test image; b) a data storage device that stores a probabilistic atlas with probabilities for the presence of the target organ at different locations relative to a bounding region of the target organ; and c) a data processor with access to the test image and the probabilistic atlas, programmed to: i) identify, at least provisionally, a location for a bounding region of the target organ in the test image; and ii) use the probabilities in the probabilistic atlas to segment the target organ in the test image.

Optionally, the data processor is programmed to use the probabilities in the probabilistic atlas to find a seed voxel in the bounding region of the test image that is likely to belong to the target organ, and to use a region-growing algorithm to grow a segmentation mask of the target organ from the seed voxel.

Optionally, the data processor is programmed to use a cost function based at least in part on the probabilities in the probabilistic atlas to grow the segmentation mask of the target organ from the seed voxel.

There is further provided, according to an exemplary embodiment of the invention, a method of segmenting an organ in a medical image, the method comprising a) identifying one or more seed voxels as being within the organ in the medical image; and b) using a region-growing algorithm to generate a segmentation mask of the organ from the one or more seed voxels, by running the region-growing algorithm on a data processor, wherein the region-growing algorithm uses a cost function for voxels that depends both on one or more local voxel characteristics, and on a total volume reached so far in the region-growing, the cost function being higher for the total volume greater than a greatest complete volume expected for the organ than for the total volume less than a smallest complete volume expected for the organ.

There is further provided, according to an exemplary embodiment of the invention, a system for segmenting an organ in a medical test image, the system comprising: a) an input device that receives a digital medical test image showing the organ; and b) a data processor with access to the test image, programmed to generate a segmentation mask of the organ in the test image, using a region-growing algorithm with a cost function that depends both on one or more local voxel characteristics, and on a total volume reached so far in the region-growing, the cost function being higher for the total volume greater than a greatest complete volume expected for the organ than for the total volume less than a smallest complete volume expected for the organ.

There is further provided, according to an exemplary embodiment of the invention, a method of segmenting a target object in a medical image, with no or reduced leaking into other adjacent objects in the image, the method comprising: a) providing a mask of the target object in the image; b) eroding the mask a first time by a number n of voxels; c) dilating the mask a first time, by n voxels after eroding the mask the first time; d) removing from the mask one or more components of voxels of suspected leaking, the component(s) satisfying one or more removal criteria, after eroding the mask the first time, and either before or after dilating the mask the first time; e) dilating the mask a second time by a number m of voxels, only into voxels that were eroded in (b), after removing the one or more components of voxels of suspected leaking, and after dilating the mask the first time; f) eroding the mask a second time, by m voxels, after dilating the mask the second time, only from a portion of the mask's surface that is adjacent to voxels that were in the mask as provided in (a), but have since been removed or eroded; and g) removing from the mask voxels, if there are any, that were not present in the mask as provided in (a), at any time after dilating the mask the first time; wherein the method is performed by a data processor.

Optionally, providing a mask of the target object comprises identifying one or more seed voxels as being within the target object in the image, and using a region-growing algorithm to grow the mask from the one or more seed voxels.

Optionally, the removal criterion is being disconnected in the mask from all of the one or more seed voxels.

There is further provided, according to an exemplary embodiment of the invention, a system for segmenting a target object in a medical test image, the system comprising: a) an input device that receives a digital medical test image showing the organ; and b) a data processor with access to the test image, programmed to segment the organ in the test image by: i) providing a mask of the target object in the image; ii) eroding the mask a first time by a number n of voxels; iii) dilating the mask a first time, by n voxels after eroding the mask the first time; iv) removing from the mask one or more components of voxels of suspected leaking, the component(s) satisfying one or more removal criteria, after eroding the mask the first time, and either before or after dilating the mask the first time; v) dilating the mask a second time by a number m of voxels, only into voxels that were eroded in (ii), after removing the one or more components of voxels of suspected leaking, and after dilating the mask the first time; vi) eroding the mask a second time, by m voxels, after dilating the mask the second time, only from a portion of the mask's surface that is adjacent to voxels that were in the mask as provided in (i), but have since been removed or eroded; and vii) removing from the mask voxels, if there are any, that were not present in the preliminary mask as provided in (i), at any time after dilating the mask the first time.

There is further provided, according to an exemplary embodiment of the invention, a method of segmenting a plurality of target objects in a medical image, the method comprising: a) identifying one or more seed voxels for each of the target objects; b) generating a binary segmentation mask of each of the target objects from that object's one or more seed voxels, at least using a region-growing algorithm, wherein growing the masks of different target objects is done independently, without regard to whether or not there is any overlap between the masks of the different target objects; c) identifying a non-empty overlap region of the masks of a set comprising at least some of the target objects; and d) generating a revised mask of each of the one or more target objects by assigning each of at least some voxels in the overlap region to only one of the target objects in the set;

wherein the method is performed by a data processor.

Optionally, the method further comprises displaying, storing or transmitting the revised mask, or information obtained from the revised mask, or one or more of the target objects.

Optionally, assigning a voxel in the overlap region to one of the target objects comprises, for voxels that were added to the mask by the region-growing algorithm: a) determining a measure of average cost function along a path taken by the region-growing algorithm from one of the one or more seed voxels to the voxel being assigned, for each target object in the set; and b) assigning the voxel to the target object for which the measure of average cost function is lowest.

Optionally, assigning at least some voxels in the overlap region to one of the target objects comprises: a) determining the target object in the set for which the mask of the target object most fully surrounds the overlap region; and b) assigning at least a portion of the voxels in the overlap region to the target object for which the mask most fully surrounds the overlap region.

Optionally, assigning at least some voxels in the overlap region to one of the target objects comprises: a) comparing the volume of the mask of each target object in the set to an expected volume for that target object; and b) if the volume of the mask is sufficiently smaller than an expected volume of the target object for all but one of the target objects in the set, then assigning all of the voxels of the overlap region to that target object.

There is further provided, according to an exemplary embodiment of the invention, a system for segmenting a plurality of target objects in a medical test image, the system comprising: a) an input device that receives a digital medical test image showing the organ; and b) a data processor with access to the test image, programmed to segment the organ in the test image, by: i) identifying one or more seed voxels for each of the target objects; ii) generating a binary segmentation mask of each of the target objects from that object's one or more seed voxels, at least using a region-growing algorithm, wherein generating the masks of different target objects is done independently, without regard to whether or not there is any overlap between the masks of the different target objects; iii) identifying a non-empty overlap region of the masks of a set comprising at least some of the target objects; and iv) assigning each of at least some voxels in the overlap region to one of the target objects in the set.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The methods described herein are generally designed only for use by a computer, and may not be feasible or practical for performing manually, by a human expert. A human expert who wanted to manually perform similar tasks, such as segmenting a target organ in a medical image, would most likely use completely different methods, making use of expert knowledge and the pattern recognition capabilities of the human brain, which would be vastly more efficient than manually going through the steps of the methods described herein.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings.

DESCRIPTION OF SPECIFIC EMBODIMENTS OF THE INVENTION

Figure 1:
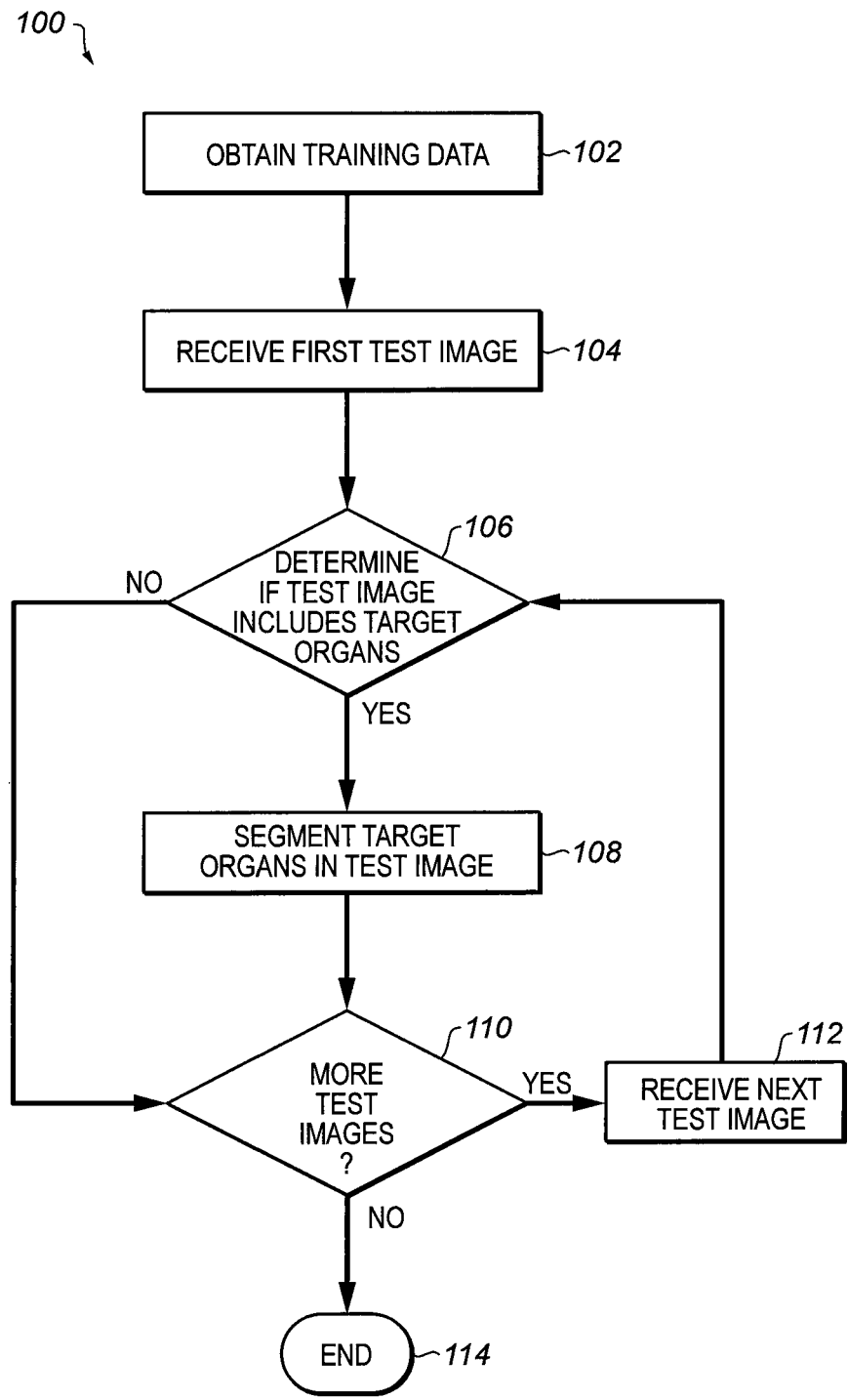
FIG. 1 is a flow chart showing a method of obtaining training data from training medical images, and using the training data to segment one or more target organs in a test medical image, according to an exemplary embodiment of the invention.

Reference is made to U.S. Provisional application U.S. Ser. No. 62/217,987 provisionally filed on Sep. 14, 2015, entitled IMAGE PROCESSING OF ORGANS DEPEND- ING ON ORGAN INTENSITY CHARACTERISTICS in the name of Tiferet T. Gazit, incorporated herein by reference in entirety.

The present invention, in some embodiments thereof, relates to segmenting an organ or other structure in a medical image and, more particularly, but not exclusively, to automatically detecting and segmenting a target organ. Although the examples described herein, and the tests of the method made by the inventors, all involve three-dimensional CT images, the method can also be used with medical images produced by other modalities, such as MRI, with appropriate changes in the units used for intensity. The method can also be used for two-dimensional medical images, for example a single slice of a CT or MRI image.

An aspect of some embodiments of the invention concerns a method of segmenting a target organ in a medical test image, by using a probabilistic atlas for the location of the target organ relative to a bounding region for the target organ. The probabilistic atlas is constructed by looking at the location of the target organ relative to its bounding region in a set of many other images, referred to as training images, in which the location of the target organ has already been identified, for example manually identified, and finding the probability that a given voxel, relative to the bounding region, will be part of the target organ. This may be done, for example, by aligning the bounding regions of the target organ in the different training images, if necessary changing the scale of the image and/or changing the number of voxels along one or more of the principle axes, so that the bounding regions all have the same dimensions and the same number of voxels along each of the principal axes, and then determining, for each voxel location, in what fraction of images that voxel is part of the target organ. In effect, the probabilistic atlas provides statistical information on the shape and orientation of the target organ with respect to the principal axes of the body, in a large number of subjects.

The bounding region is, for example, a rectangular box oriented along the principal axes of the body, or some other standard shape, for example an elliptical cylinder or an ellipsoid oriented along the principal axes, that is as small as possible in each of its principal directions while still including all of the organ. Alternatively, the bounding region extends further and/or not as far, in one or more directions, than the smallest region of that shape that will still include all of the organ, but the dimensions of the bounding region are based on the smallest bounding region that will still include all of the organ. For example the bounding region is the smallest bounding region of that shape that will still include all of the organ, transformed by an affine or warping transformation and/or by a translation, optionally always the same transformation and translation, and optionally with the bounding region still including all or substantially all of the organ, which may result in the probabilistic atlas having effectively the same information as if the bounding region were the smallest bounding region of that shape that will still include the organ, with the two atlases related to each other by applying the transformation and translation. For clarity of presentation, it will be assumed herein that the bounding region is the smallest bounding region of that shape that includes all of the organ, with the understanding that this definition of bounding region can be extended to more general cases that are effectively equivalent.

This kind of probabilistic atlas serves a different purpose from other kinds of probabilistic atlases, which give the probability of a voxel belonging to a target organ, as a function of the voxel's position relative to the whole body. Such probabilistic atlases provide statistical information on the overall location of the target organ in the body, rather than on the shape and orientation of the target organ. Other kinds of probabilistic atlases do provide information on the shape of the organ, but they do not accomplish this by finding the probability of the organ being present at a location relative to the bounding region of the organ. For example, a probabilistic atlas may be generated in which the different training images of the target organ are aligned by finding the rigid transformation that maximizes their cross-correlation with the test image. Such methods produce different information about the shape of the target organ than if the training images were aligned by aligning the bounding regions of the target organ, and furthermore, using the test image to align the training images requires that the test image be known before the atlas can be constructed. In general, if training images are aligned in some other way, rather than by aligning the bounding regions, when generating the atlas, then the atlas may extend well beyond the bounding region of the organ, with probabilities falling off only gradually.

It is also possible to use probabilistic atlases in a very different way, finding a mean or baseline shape of the target organ in a series of training images, and then finding a series of warping modes that can transform the shape of the target organ, and the probabilities of the different warping modes occurring in the training images. Such an atlas may be very difficult to construct, requiring an enormous number of training images to get good statistics on all the warping modes.

A probabilistic atlas that is created by aligning the bounding regions of the target organ in the different training images will generally have a different appearance than a probabilistic atlas that is generated by aligning the training images in a different way, such as using one of the alignment methods described above. For example, if the atlas is created by aligning the bounding regions of the target organs, the probability will generally have its steepest gradient near an edge of the bounding region, near a location where the organ is tangent to the edge of the bounding region, and where the surface of the organ has relatively low curvature. At such a location, the probability p will rise steeply from its value of 0 at the edge. The gradient in probability will be greatest, for example, for probability below 0.2, or below 0.1. The closest approach of the $p=0.1$ surface, or the $p=0.2$ surface, to the edge of the bounding region, will be less than 20%, or less than 10%, or less than 5%, or less than 2%, of the closest approach of the $p=1$ surface, or the $p=0.9$ surface, or the $p=0.8$ surface, or the point or surface of maximum p, to the edge. The numbers will depend, in general, on how sharply curved the surface of the organ is at the point where it is tangent to the bounding region, and on how much the location of the tangent point varies among the different training images. Generally, the gradient in probability is expected to be steepest when the surface of the organ has low curvature at the tangent point, and when the location of the tangent point does not vary very much between training images. For other types of probabilistic atlases, the gradient in probability is likely to be relatively low at low values of p, and to be greatest at intermediate values of p, for example between $p=0.1$ and $p=0.9$ or between $p=0.2$ and $p=0.8$.

Optionally, the probabilistic atlas is generated from a wide enough variety of training images, with a great enough variation in shape of the organ, that a significant fraction of voxels in the bounding region have intermediate values of probability, rather than almost all voxels having probability close to 1 or close to 0. For example, optionally at least 10% of the voxels in the bounding region, or at least 15% of the voxels in the bounding region, or at least 20% of the voxels in the bounding region, have probability between 0.2 and 0.8.

Optionally, the probabilistic atlas is generated independently of the test image. Optionally, the probabilistic atlas is generated before the test image is received by a computer that is segmenting the target organ in the test image. Optionally, the probabilistic atlas is generated by a different computer, which does not receive the test image before generating the probabilistic atlas, or which never receives the test image. For example, the probabilistic atlas is optionally generated in advance by a producer of segmentation software, and is sold together with the software to an end user, who then uses the probabilistic atlas and the software to segment test images of interest to the user, possibly test images that are newly acquired by the user.

In order to segment the target organ in a test image, the location of the bounding region for the target organ, or at least an approximate location, is identified in the test image, at least provisionally, with a more accurate location optionally found later. The probabilistic atlas can then be used to segment the target organ, for example by finding voxels in the test image that are particularly likely to belong to the target organ.

Optionally, finding voxels that are particularly likely to belong to the target organ is based not only on the position of the voxels and the probabilistic atlas, but also on the voxels having intensity values in a range expected for the target organ. Optionally, one or more of the voxels, considered likely to belong to the target organ, are used as a seed for segmenting the organ using a region growing algorithm, for example a fast marching algorithm. Optionally, a cost function used by the region growing algorithm is also based, at least in part, on a probability that a voxel belongs to the target organ, according to the probabilistic atlas. Optionally, once the target organ is initially segmented, the segmentation is used to refine the assumed location of the bounding region for the target organ, and the segmentation procedure is iterated one or more times using the new assumed location of the bounding region.

Figure 6:
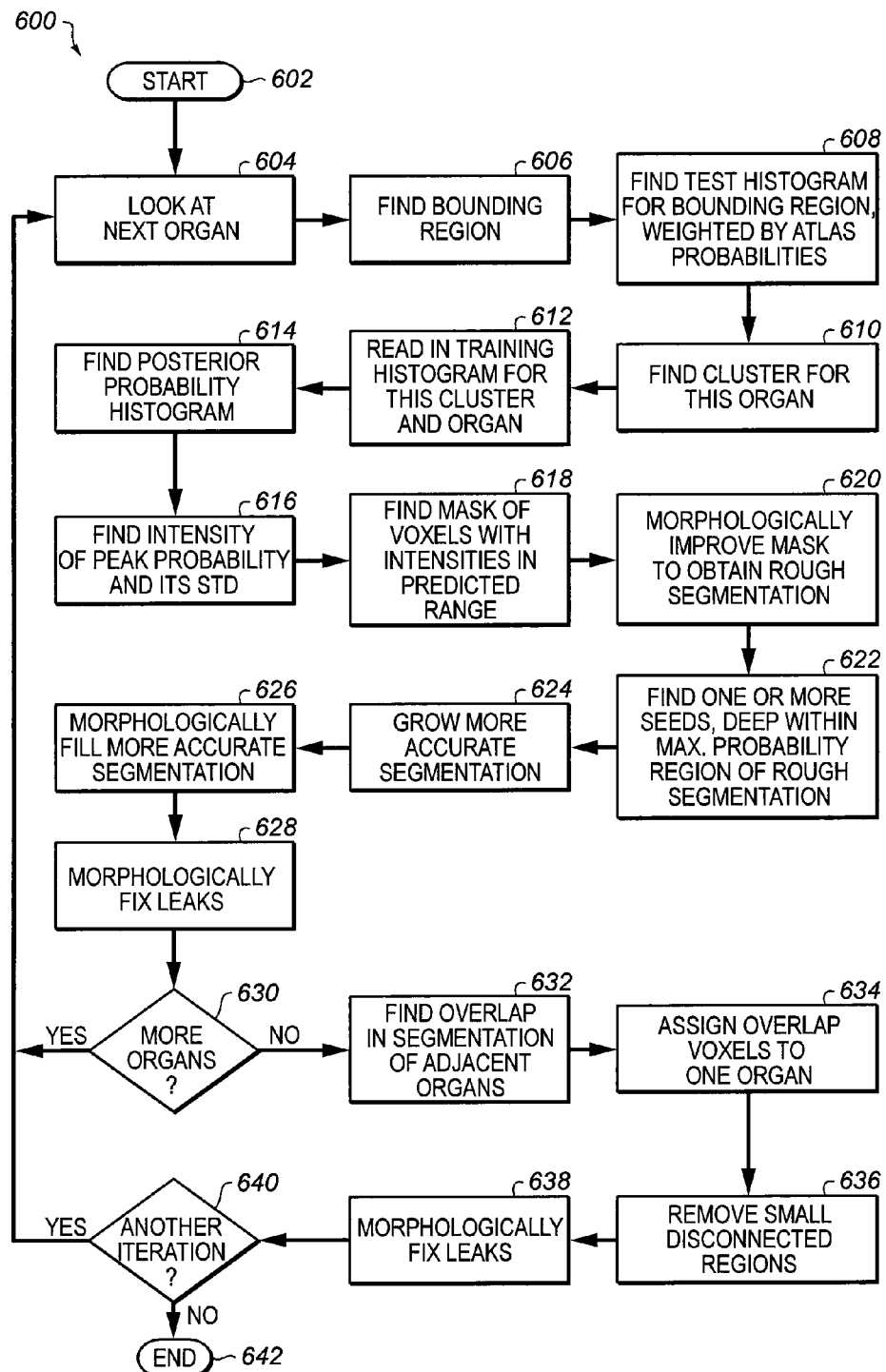
FIG. 6 is a flow chart showing a method of segmenting one or more target organs in a medical image, according to the method of FIG. 1 and in particular the method of FIG. 5B.

As used herein, segmenting an object, such as a target organ, in an image, means generating a segmentation mask, sometimes simply called a mask, for the object in the image. A segmentation mask assigns a value to each voxel in the image, indicating whether or not the voxel belongs to the object, or indicating how likely the voxel is to belong to the object, or a propensity for the voxel to belong to the object. Optionally, the segmentation mask is a binary segmentation mask, in which each voxel is assigned only one of two values, indicating whether or not the voxel belongs to the object. For example, a voxel is assigned a value of 1 to indicate that it belongs to the object, and a voxel is assigned a value of 0 to indicate it does not belong to the object. Alternatively, the segmentation mask assigns any of more than two values to each voxel, or any of a continuous range of possible values to each voxel. For example, a probabilistic segmentation mask assigns to each voxel in the image a value in the range from 0 to 1, to indicate a probability that the voxel belongs to the object. In the examples described herein, the segmentation mask is generally assumed to be a binary segmentation mask, and some methods described herein are especially applicable for binary segmentation masks. For example, reassigning voxels in an overlap region between segmentation masks of two different organs, described below in 634 of FIG. 6, is especially applicable for the case of binary segmentation masks, where an overlap between two segmentation masks may indicate that at least one of the masks has errors in it.

Optionally, for any of the methods described herein, where a segmentation mask is generated, the segmentation mask is then displayed to a user, stored in a computer memory or digital media for later use, or transmitted, for example to a remote user or computer. For example, the segmentation mask is optionally combined with the image, and rendered as a 2-dimensional or 3-dimensional display, with the target organ or object marked or labeled in some way, and displayed to a user, such as a radiologist, who can then see exactly where the target organ or object is located in the image, and can examine its appearance. Alternatively, the segmentation mask itself is not displayed, stored, or transmitted, but is used to obtain information that is displayed, stored, or transmitted. For example, if the spleen is segmented, then optionally the segmentation software uses the segmentation mask of the spleen to find the volume of the spleen, and to determine whether the spleen is larger than expected in a healthy patient. The software then optionally displays or transmits a warning to one or more medical personnel responsible for that patient, informing them that the patient may have an enlarged spleen, which may be indicative of a hitherto unsuspected disease. Optionally, this is done without ever displaying, transmitting, or even storing the segmentation mask of the spleen, or an image with the spleen marked.

In some embodiments of the invention, whether or not a probabilistic atlas of the target organ relative to the bounding region is used in segmenting the target organ, training images including the target organ are divided into clusters, each cluster corresponding to a different set of contrast characteristics due to different parameters of contrast agent use, and each test image is assigned to one of the clusters, for purposes of determining what voxel intensities and intensity gradients are likely to be found in the target organ. Other embodiments of the invention segment a target organ without using either a probabilistic atlas of the target organ relative to the bounding region, or clustering of training images with different contrast characteristics. The following three paragraphs describe embodiments of the invention that need not use either a probabilistic atlas or clustering, but have other features that make them inventive.

An aspect of some embodiments of the invention concerns segmenting an organ in a medical image using a region growing algorithm, with a cost function that depends on the total volume grown so far, rather than only on local characteristics of the voxels, with the cost function being greater when the total volume is greater than a greatest expected volume for the organ, than it is when the total volume is less than a smallest expected volume for the organ. This feature may make it less likely that the growth algorithm will leak very far into a large neighboring organ with local voxel characteristics that are similar to those for the organ being segmented.

An aspect of some embodiments of the invention concerns a method of segmenting a target organ in a medical image, using a region growing algorithm, with reduced leaking into neighboring organs. The method could potentially also be used for segmenting other objects in images, even in non-medical images. The method first applies a morphological opening, an erosion followed by a dilation of the same size, to a mask of the segmented organ. This procedure disconnects small leaks into neighboring organs, which were connected to the main part of the mask by a narrow neck before the morphological opening was performed. Disconnected regions that are believed to be part of leaks, and not part of the targeted organ, are removed from the mask. This can be achieved, for example, by assuming that the seed that the region growing algorithm begins from is in the target organ, and regions that are disconnected from the seed after the morphological opening are removed from the mask. The remaining mask is then dilated a second time, but only into voxels that were in the original mask, and this dilation expands the mask back to its original boundaries, in places that did not leak, and part way up any narrow neck that connected it to a disconnected region that was removed. The mask is then eroded again, only from parts of the surface that are adjacent to disconnected regions that were removed, which removes the narrow necks from the mask. Any voxels not in the original mask are also optionally removed.

An aspect of some embodiments of the invention concerns segmenting two or more organs or other objects in a medical image by independently growing a mask for each organ from a seed using a region growing algorithm, identifying an overlapping region of two or more of the masks, and assigning at least some voxels in the overlap region to only one of the organs. Optionally, each voxel is assigned to the organ for which an estimate of the average value of the cost function, along the path taken from the seed to that voxel, is lowest. Optionally, if the mask for one of the organs almost completely surrounds the other organ, then the overlap voxels are assigned to the surrounding organ, and the surrounded organ is deleted. Optionally, if the mask for only one of the organs is an expected volume for that organ, and the mask for the other organ is much smaller than expected, then voxels in the overlap region are assigned to the organ with the expected volume, and the other organ is deleted.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 3:
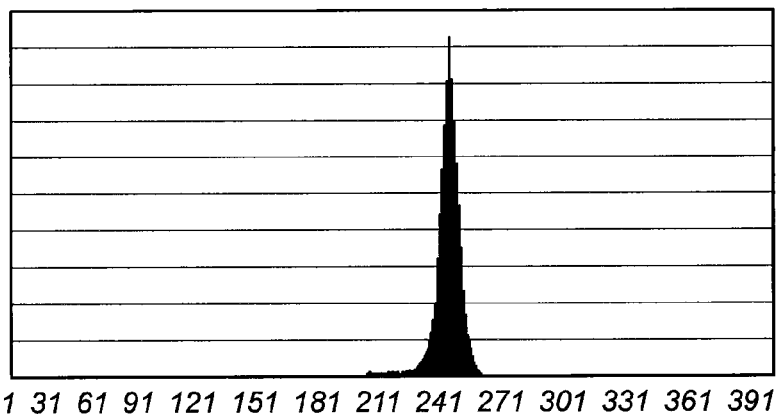
FIG. 3 shows examples of intensity histograms obtained according to the method of FIG. 2.
Figure 4:
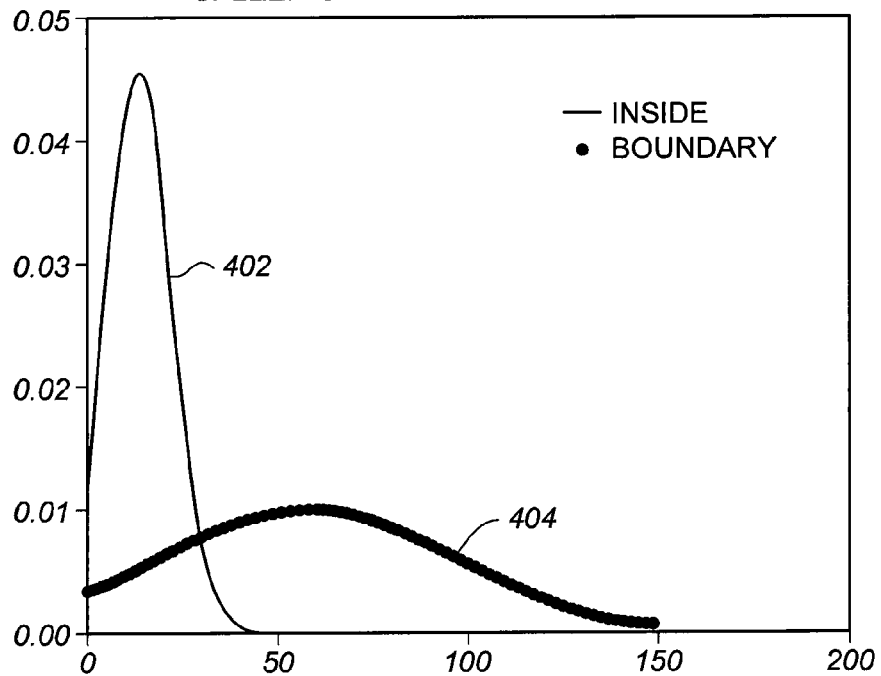
FIG. 4 shows examples of intensity gradient distributions for an interior of an organ and for a boundary of an organ, obtained according to the method of FIG. 2.

Referring now to the drawings, FIG. 1 shows a flow chart 100 illustrating an overview of a method of automatically segmenting one or more target organs in medical images, according to an exemplary embodiment of the invention. At 102, training data is obtained from training images. Optionally a relatively large number of training images are used, that can provide good statistics on the appearance of the target organs in a population of patients. The training data includes information on the shape and orientation of the organ, as described for example by a probabilistic atlas of the location of the organ relative to a bounding region of the organ, as well as the volume of the organ, and the distribution of intensity values and gradients for the organ and for nearby voxels outside the organ. Details on the method of obtaining training data for each target organ are given below in FIG. 2, and examples of such training data are shown in FIGS. 3, 4, and 5. Training data for different target organs is obtained either in parallel or consecutively, optionally using the method of FIG. 2 for each target organ of interest. At 104, the first of the test images to be segmented is received. At 106, a determination is made as to whether the test image being examined covers the part of the body that would include the target organs, for example the abdomen. Optionally, this determination is made automatically by computer, with no user intervention, for example using the method described in U.S. Pat. No. 8,170,306 to Yu et al, or any other known method of automatically determining the part of the body covered by the field of view of a medical image. If the test image being examined is expected to include the target organs, then the target organs are automatically segmented in the test image, at 108. The method of segmenting the target organs in the test image, using the training data obtained at 102, is described below in FIG. 6. After segmenting the target organs in the test image, the method determines, at 110, if there is another test image to be examined. This is done immediately after 106, if it is determined that the image being examined at 106 is not expected to include the target organs. If there is another test image, then it is received at 112, and a determination is again made, at 106, as to whether the test image is expected to include the target organs or not. If there are no more test images to be examined, the method ends at 114. In some embodiments of the invention, 106 and 108 are performed for some or all of the different test images in parallel, rather than consecutively as shown in FIG. 1.

It is noted that the method of flow chart 100 differs from some other methods described above, because in flow chart 100, the training data, which includes a probabilistic atlas in some embodiments of the invention, is generated at 102, before any test images are received at 104, and independently of what test images are to be used. Once the training data is generated, it may be used in segmenting any test images that are received. In some other methods, a different probabilistic atlas is generated for each test image received, adapted specifically for that test image, using only those pre-stored images in which the organs are similar in appearance to that test image. In addition, as noted above, the pre-stored images may be each registered to the test image, before using them to generate the probabilistic atlas. In either of these cases, the probabilistic atlas used for each test image can be generated only after the test image is received.

This difference between these other methods and the method of flow chart 100 may be necessitated by a different purpose to which the probabilistic atlas is used. In the method of flow chart 100, specifically in the embodiment of the method shown in FIG. 5B, the atlas is used primarily to find a seed voxel which is very likely to belong to the target organ, which is then used with a region-growing algorithm to grow a segmentation mask of the target organ from the seed voxel. The atlas is also used to find a core region of the organ from which the organ intensity distribution can be learned. A probabilistic atlas based on the location of an organ relative to its bounding box is particularly useful for reliably distinguishing a core region of voxels that belong to the target organ, from voxels that may belong to an adjacent organ with similar image intensities, which overlaps the bounding region of the target organ, but is located in a different part of the bounding region of the target organ. For example, the stomach has image intensity similar to the spleen, and overlaps a large part of the bounding region of the spleen, but is found in a different part of the spleen's bounding region than the spleen is. For these purposes, it is important for the probabilistic atlas to have at least some voxels that have a very high probability of belonging to the target organ, and it does not matter very much if many other voxels in the probabilistic atlas have intermediate probabilities. Typically, in tests done by the inventor with the liver, spleen, and kidneys as target organs, more than 15%, or more than 20%, or more than 25% of the voxels in the probabilistic atlas have intermediate probabilities, between 20% and 80%, of belonging to the target organ.

These other methods, on the other hand, may use the probabilistic atlas directly to decide which voxels belong to the target organ and which do not, so it is more important that voxels in the probabilistic atlas, as many as possible, will have probability close to 100% or close to 0%. To achieve this goal, only training images that are similar in appearance to the test image may be used in constructing the atlas, and this precludes preparing the atlas in advance, without knowing what test image it will be used for.

Another possible consequence of these methods of using the probabilistic atlas directly, together with information about expected intensity values, to decide which voxels belong to the target organ and which do not, is that it may be more difficult to segment target organs in images where contrast agent is used. When contrast agent is used, it is more likely that the intensity of voxels in the target organ will be very non-uniform. This is generally not a serious problem if the only goal is to find one or a few seed voxels that are very likely to belong to the target organ, since these can all be located in a uniform intensity core region of the target organ, but it is more difficult if the goal is to find all the voxels that belong to the target organ, with high reliability.

The ability to generate a probabilistic atlas in advance, without knowing what test image it will be used for, gives the method of flow chart 100 some great potential advantages over the method of custom-making a different atlas for each test image. With the method of flow chart 100, the training data is optionally generated off-line, in advance, so that its generation requires neither time nor computational resources on the user's end. The training may be carried out on a large collection of training images, none of which need to be made available to the user. The pre-generated training data may optionally be supplied to the user together with the software that runs the organ detection and segmentation. It is therefore possible to create a full division between the training module (1204 of FIG. 12) and the selection and segmentations modules (1212 and 1208 of FIG. 12), such that the training module receives segmented training images and generates the training data at one site and one time, and the selection and segmentation modules receive only the training data and the test images, and may be run at a completely different site and at any later time. With a method that generates a different atlas for each test image, on the other hand, the atlas cannot be generated in advance, and its generation requires time and computational resources for each test image. In addition, all the training images must be stored and accessed by the segmentation module on the user's computer, which is particularly problematic for medical images, since they are not allowed to be shared without special permission and careful compliance with legal procedures, which differ from country to country, to insure that they cannot be identified and to protect patient privacy.

Some prior art may use a probabilistic atlas to segment an anatomical structure, such as an organ, in a medical image, though not a probabilistic atlas for the location of the structure relative to its bounding region. Some methods also differ from the method shown in FIG. 5B, because they do not use the atlas to find a seed for a region-growing algorithm, and/or do not use a region-growing algorithm at all. Rather, a method may be used, similar to an energy functional method, in which a cost function, defined as a sum over all voxels in the image being segmented, is minimized, in order to segment the anatomical structure, and this method may not require finding a seed voxel that is known to be in the structure that is being segmented.

Obtaining Training Data

Figure 2:
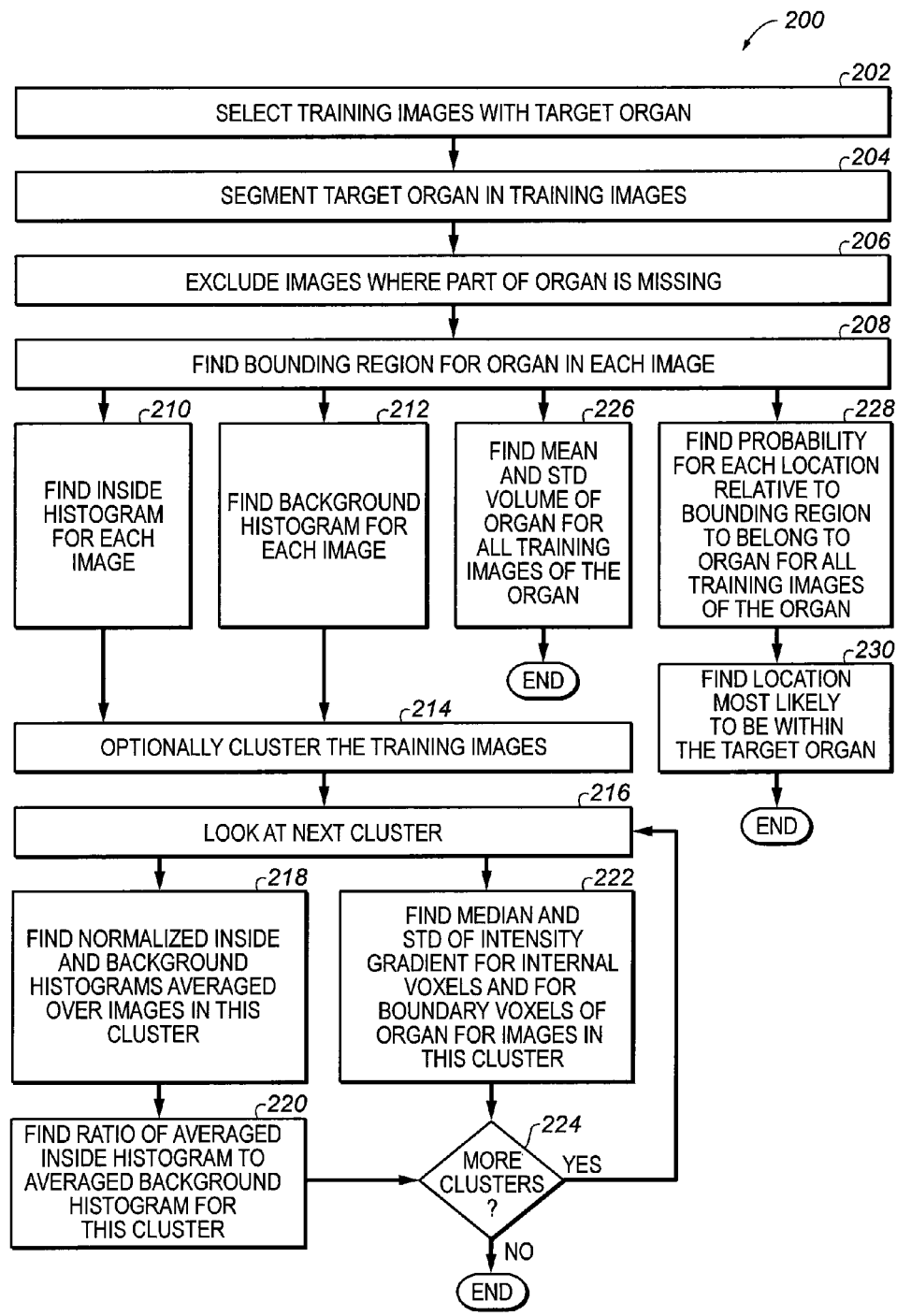
FIG. 2 is a flow chart showing a method of obtaining intensity histograms and a probabilistic atlas, for a target organ, from training images, according to the method of FIG. 1.

FIG. 2 shows a flow chart 200, with more details on the method of obtaining training data for a particular target organ at 102 of FIG. 1, according to an exemplary embodiment of the invention. At 202, a set of training images is selected, which include the target organ. Optionally, training data for more than one target organ is obtained from the same set of training images. It is potentially advantageous if a large enough set of training images is used to provide good statistics on the appearance of the target organ in different patients, and under a range of imaging conditions, especially if the test images that the training data is to be used with are also expected to be made under such a range of imaging conditions. For example, 100 different CT images of the abdomen are used, made with a variety of different CT imaging systems, run with a range of different settings and protocols, with a range of resolutions and noise levels, ordered for a variety of reasons, from different patients, some of them exhibiting diseases that are expected to occur in test images, and that may change the appearance of affected organs. But optionally, images in which the target organ has a very abnormal appearance, due to disease or surgery, are not included among the training images, since such abnormal organs are expected to occur only rarely in test images, and including them among the training images might make the training data less useful for segmenting the great majority of test images. Optionally, some of the training images use contrast agent and some do not, with different types of contrast agent, introduced orally or intravenously or both, different amounts of contrast agent, and different timing of the image after the contrast agent was introduced, in different training images.

At 204, the target organ is segmented in each training image. Optionally, the segmentation is done manually by an expert, or semi-manually. It is advantageous for the segmentation of the target organ in the training images to be accurate, in order to obtain training data that is accurate and hence useful for later automatic segmentation of test images. At 206, training images that only include part of the target organ are excluded. Optionally that is done before the organ is segmented in training images.

At 208, a bounding region is found for the target organ, in each training image. The bounding region is, for example, a rectangular box, oriented along the principle axes of the body in the medical image, that extends in each principle direction between the maximum and minimum value of the coordinate for that direction, for any voxel in the organ. Such a box is the smallest rectangular box, oriented along the principle axes, that includes all of the voxels in the organ. The bounding region is not found in order to specify the location of the target organ relative to the entire body, but in order to specify the orientation, shape and size of the organ, by finding the location of the organ relative to the bounding region. For this purpose, the bounding region need not be a rectangular box oriented along the principle axes of the body, but can be any standard shape specified by relatively few parameters, for example a rectangular box oriented in a different fixed way relative to the principle body axes, or a circular cylinder or elliptical cylinder oriented along the principle axes of the body or in some other fixed way, or an ellipsoid, or a parallelepiped with fixed angles or parameterized angles, or a prism with cross-section of specified shape or a shape specified by one or a few parameters. Using a bounding region that is a rectangular solid, oriented along the principle body axes, has the potential advantage that it is easy to define, in the case where the image consists of voxels arranged in a Cartesian coordinate system oriented along the principle body axes, as in usually true of medical images. The inventors have found that using such a bounding region produces good results, and for convenience it will be assumed in the description that follows that the bounding region is such a rectangular box. The bounding region for a target organ in a given image can then be found by finding the maximum and minimum values of each coordinate, for any voxel in the target organ. However, it should be understood that any other form of bounding region can be used instead, and it will be clear to one of skill in the art how to implement the methods described herein using a different form for the bounding region.

Intensity histograms are then found for each image, at 210 and 212, in parallel, or consecutively. In the case of CT images, the intensity of a voxel is typically specified in Hounsfield units (HU). Other intensity units are used in different imaging modalities, for example in MRI images. The method has been implemented by the inventors for CT images, and will be described herein with reference to CT images, but the method could be used with other imaging modalities as well. Optionally, the images are smoothed, for example to reduce noise, using any known image smoothing algorithm, before finding the intensity histograms. However, the inventors found that, at least for the CT images that were used, better results were achieved without smoothing the images.

At 210, an inside intensity histogram is found, for each image, for the voxels inside the target organ. At 212, a background intensity histogram is found, for each image, for the voxels in the bounding region that are outside the target organ. Optionally, a histogram of the intensities of all the voxels in the bounding region is also found, for each image. Optionally, the histograms for all the training images are each normalized, for example to have an integrated value of 1, so that they can be meaningfully compared to each other, and so that histograms from different images can be meaningfully averaged together, even if the images have different resolutions and hence different numbers of voxels in a given volume.

At 214, the histograms from the different images are optionally used to sort the images into clusters representing different contrast characteristics, due to different types of contrast agent, and/or different degrees and timing of contrast agent use. Such clustering is especially useful if the test images for which the training data is intended, and the training images themselves, have a wide variety of contrast characteristics, which are not necessarily learned easily from data associated with the images.

The following method has been found by the inventors to be suitable for sorting the training images into clusters. Alternatively, other known method of clustering can be used. Optionally, the normalized inside intensity histograms are used for clustering the training images. Alternatively, a different choice of histogram is used, for example the normalized intensity histogram of all the voxels in the bounding region, for each image.

The clustering is accomplished by treating each training histogram as a vector, with each histogram bin being treated as a single coordinate in the vector. Each such vector forms a single sample for the clustering algorithm.

K-means clustering is used, optionally with four clusters, optionally with a Bhattacharyya clustering distance measure (defined in Bhattacharyya, A., "On a measure of divergence between two statistical populations defined by their probability distributions," Bulletin of the Calcutta Mathematical Society 35: 99-109 (1943)), which is known to work well for probability functions such as those represented by these histograms, and optionally with ten random clustering re-initializations, stopping the clustering algorithm when the change in distance between iterations is below a threshold, for example $10^{-8}$. For each initialization, the input samples are optionally split into four random sets of roughly equal size, which are used to initialize the k-means. In this manner ten potentially different clusterings of the input samples are achieved. Optionally the clustering is selected that gives the most samples in its smallest cluster, which has the potential advantage of avoiding clusters with very few samples, representing only a few training images, which may lead to over-learning of intensity statistics. Alternatively, other methods of combining the ten results to create a final clustering are used, such as using a voting mechanism. The number of clusters, and other parameters of this k-means clustering, were chosen experimentally, by dividing 100 training studies into five exclusive divisions of 80 training and 20 test sets and finding the parameter setting that led to the best organ segmentation, of the liver, the spleen, and the left and right kidneys in the resulting test images. Visually, the four clusters correspond roughly to organs with no contrast agent, organs with very weak contrast, organs with stronger contrast, and organs with very strong contrast. In the case of the kidneys, the clustering separated kidneys with no contrast, kidneys with weak contrast approximately evenly distributed throughout, kidneys with stronger contrast and some gradient between the inner and outer regions, and kidneys with very strong contrast along the outer surface and a large gradient between the inner and outer regions. In these tests, it was visually verified that the clustering algorithm successfully separated the test organs into such visually-distinct clusters, and also that new previously unseen images of organs were correctly mapped into the expected cluster, based on their visual appearance.

For each cluster, an average or representative histogram is found from intensity histograms for the training images in that cluster, and saved as part of the training data. For example, the average or representative histogram is optionally the mean of the normalized intensity histograms of the voxels in the bounding region for all the training images in that cluster. Alternatively, the average or representative histogram is the mean of the normalized inside histograms of the training images in that cluster, or is based on some combination of inside histograms and histograms of the whole bounding region. This average or representative histogram is sometimes referred to as the "cluster center" and is used to assign test images to one of the clusters, as described below in 512 of FIG. 5B, and in 610 of FIG. 6.

Alternatively, the training images are not clustered, but training images with different contrast characteristics are lumped together. Alternatively, only images with similar contrast characteristics are chosen for use as training images, and optionally the resulting training data is only used for test images with contrast characteristics similar to that of the training images, so there is no reason to cluster the images. If clustering is not done, then all the training images may be considered to belong to a single cluster, in the description that follows.

In the description that follows, the different clusters are processed sequentially. Alternatively, all or some clusters are processed in parallel.

At 216, one of the clusters is examined. Two types of data are generated from the training images in the cluster, at 218 and 220, and at 222, in parallel, or consecutively in any order. At 218, inside and background histograms are found, averaged over all the training images in the cluster. The ratio of the inside histogram to the background histogram is then found at 220, to produce a "training histogram" for that organ, which indicates for which relatively narrow ranges of intensity a voxel in the bounding region is relatively most likely to be in the target organ, rather than outside the target organ. Optionally the averaged inside and background histograms are normalized before taking their ratio, but this is not expected to be very important because only the shape of the training histogram is used, not its absolute magnitude.

Optionally, any reasonably smooth monotonic function of the training histogram is used instead of the training histogram, since it is generally the locations and widths of the peaks that matter when the training histogram is used to segment test images, as will be clear from the description of the method of segmenting test images in FIG. 6, below.

FIG. 3 shows a plot 300 showing an example of a training histogram, for the spleen, for a particular cluster of contrast characteristics. The horizontal axis shows the bin number for the intensity, increasing from left (lower intensity) to right (higher intensity). The bins are each 5 HU wide, and range from −990 HU to +1000 HU, while the vertical axis is arbitrary. As is typical for the organs that have been tested by the inventors, there is a very narrow peak at one value of intensity. The intensity of the spleen is fairly uniform, within each cluster of contrast characteristics, and the spleen takes up a significant fraction of the volume of its bounding region, so almost all of the voxels near that value of intensity are in the spleen rather than outside the spleen in the bounding region, and knowing the intensity at which the peak occurs in the training histogram, and the width of the peak, can be useful in segmenting the spleen in other images.

At 222 in FIG. 2, the median and standard deviation of the magnitude of the intensity gradient are optionally found, for internal voxels of the target organ, and for voxels at the boundary of the target organ, for all images in this cluster. Alternatively, the mean, mode, or another type of average value is used instead of the median, but the inventors have found that using the median works well because it is insensitive to outliers. Optionally, the magnitude of the full three-dimensional intensity gradient is used. Alternatively, for example to save computation time, only the magnitude of the intensity gradient within two-dimensional slices of the image is used, for example within axial slices, or within coronal slices, or within sagittal slices. Optionally, the distribution of the intensity gradient is normalized for each image, before averaging the distribution functions for the different images and finding the median and standard deviation of the averaged distribution function. Such normalizing will allow different images to have the same weight in finding the averaged distribution, even if they have very different resolutions and hence very different numbers of voxels in the target organ. Alternatively, the full distribution function of intensity gradients in the interior and on the boundary of the organ are kept as part of the training data, instead of or in addition to the median and standard deviation, and/or other moments of the distribution function are kept. Alternatively, information on the intensity gradients is not found at all, and are not used in segmenting the organ in test images. However, the inventors have found that using the median and standard deviation of the intensity gradient, for the interior voxels and boundary voxels, is often useful for determining the exact boundary of the target organ in a test image, since many organs have much sharper intensity gradients at the boundary than in the interior.

FIG. 4 shows a plot 400 of Gaussian curves showing the median and standard deviation of intensity gradient for voxels inside the spleen, including curve 402 for voxels in the interior of the spleen, and curve 404 for voxels on the boundary of the spleen. The intensity gradient is given in HU per millimeter. Only the two-dimensional intensity gradient within axial slices was used to find curves 402 and 404. The voxels on the boundary have much greater median and standard deviation of intensity gradient, than the voxels in the interior, and this fact can be used in segmenting the spleen using a region-growing algorithm, to indicate when the boundary may have been reached.

At 224, if there are more clusters remaining, then the next cluster is examined at 216. If there are no more clusters, then the procedure ends.

Two other types of training data are optionally found, at 226, and at 228 and 230, in parallel with the training data found at 210 to 224. Alternatively, the training data is found at 226 and/or at 228 and 230 consecutively with the training data found at 210-224, in any order.

At 226, the mean and standard deviation are optionally found for the volume of the target organ, for the training images being used for this organ.

At 228, the probability is found, for each location relative to the bounding region, that the location is in the target organ. The set of probabilities for a given organ is referred to as a "probabilistic atlas" for that organ. In order to meaningfully compare bounding regions that in general have different dimensions in different images, the bounding region in each image is mapped into the probabilistic atlas, for example by linearly scaling the different dimensions of the bounding region, using scaling factors that may be different for different directions and different images. For example, if the bounding region is a rectangular box, then the probabilistic atlas is optionally a cube of width 1, with each coordinate ranging from 0 to 1, and the width of the rectangular box in each principle direction, in each image, is optionally normalized to 1 when it is mapped to the probabilistic atlas. In this way, each location in the probabilistic atlas maps to a location in the bounding region in each image, and it is possible to find the probability that that location in each image falls within the target organ in that image. Alternatively, a different mapping is used between the bounding regions of the different images and probabilistic atlas, for example a center point of the bounding region in each image maps to a location at the center of the probabilistic atlas, and other points in the bounding region of a given image map to a point in the probabilistic atlas that is displaced from the center point by the same distance in each principle body direction.

In practice, the probability is only found for a discrete set of locations in the probabilistic atlas, which may be considered voxels of the probabilistic atlas, for example 100 voxels of uniform size across the width of the probabilistic atlas in each principle direction. In general, the different images may have different numbers of voxels in a given direction across the bounding region, and any known interpolation scheme, for example closest neighbor interpolation, is used to specify whether or not a location in a given image that maps to a given voxel in the probabilistic atlas is within the organ in that image, as opposed to being outside the organ and in the background. The probability for each voxel in the atlas is then defined, for example, as the number of training images for which the corresponding location is within the organ, divided by the total number of training images that were used for this organ. Optionally, the distribution of probabilities in the probabilistic atlas is smoothed, or otherwise processed, before using it.

At 230, using the distribution of probabilities that was found in 228, a location is optionally found in the probabilistic atlas that is deemed most likely to be within the target organ. If there is only a single location for which the probability has a maximum value, then that location is chosen. More often, there is an extended range of locations for which the probability is at its maximum value, usually 100%. In that case, the location is optionally chosen to be deep within that extended range of locations, for example at a point furthest from the boundary of the extended range of locations. Optionally, distance from the boundary is defined not in the space of the probabilistic atlas, but takes into account the ratio of scaling factors in the mapping from the images to the probabilistic atlas for the different principle directions. Although this ratio differs slightly for different images, an average value is optionally used, for purposes of defining distance from the boundary.

Figure 5A:
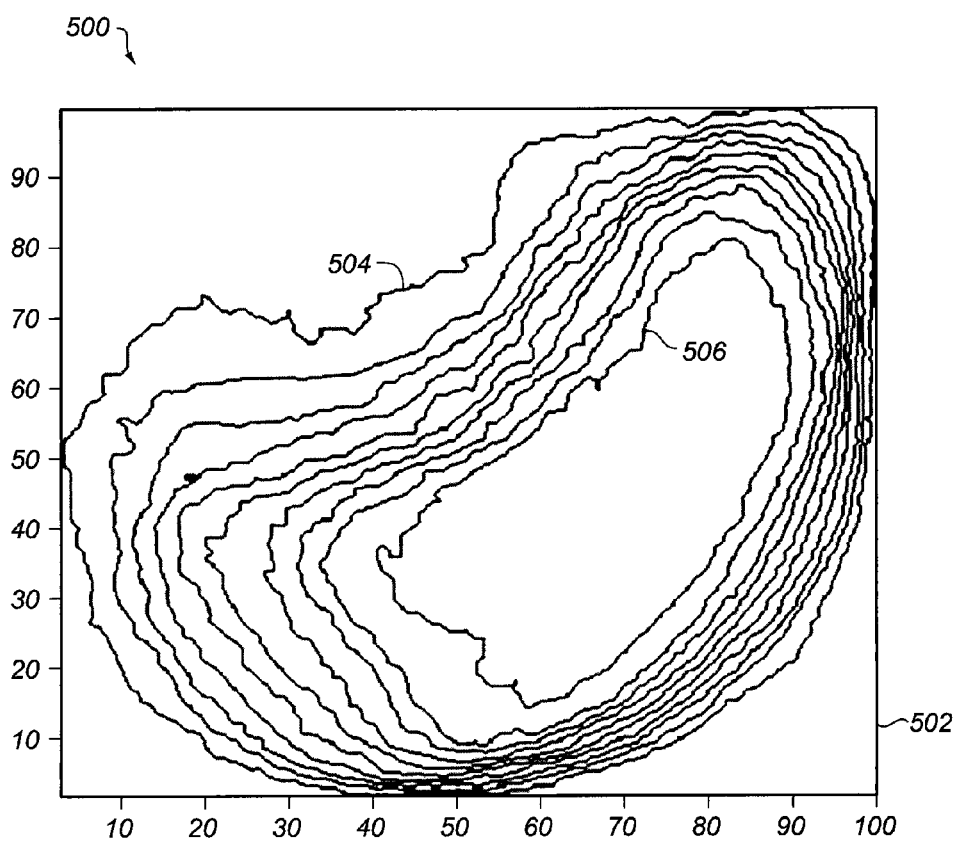
FIG. 5A shows an exemplary two-dimensional cross-section of a probabilistic atlas for an organ in a bounding region, obtained according to the method of FIG. 2.

FIG. 5A shows a plot 500 of a two-dimensional slice of a probabilistic atlas for the spleen, with a contour plot showing the probability of different locations, mapped to the bounding region of the spleen in a set of training images, being inside the spleen. Although these probabilities were calculated for a full three-dimensional probabilistic atlas, only one axial slice 502 of the probabilistic atlas is shown in plot 500, a slice going through the center of the bounding region. The slice is 100 voxels high in the vertical direction, which represents the front-back axis of the body, and 100 voxels wide in the horizontal direction, which represents the left-right axis of the body. For each training image used, 0 and 100 correspond to the limits of the rectangular box-shaped bounding region in those directions. Contour 504 is for a probability of 10%. Contour 506 is for a probability of 100%, surrounding the set of locations that were inside the spleen in all of the training images used. The fact that the 100% contour surrounds a fairly large fraction of the set of locations means that there is considerable overlap in the location of the spleen, relative to its bounding region, in all of the images. The other contours shown go from a probability of 20% to a probability of 90%, at 10% intervals. The typical shape of the spleen, seen in axial cross-section, is apparent from the contours.

FIG. 5A illustrates the characteristic appearance of a probabilistic atlas that was generated by aligning the bounding regions of the organs in the different training images. The steepest gradient in probability p occurs between the lowest probability contours shown, the p=0.1 and p=0.2 contours, near the center of the bottom edge, which is close to the point where the surface of the organ is tangent to the edge of the bounding region, for most of the training images. The gradient between the p=0.1 contour and the p=0 contour, which is not shown in FIG. 5A but which runs along the bottom edge at that location, is even steeper. At this bottom tangent point, the surface of the organ has relatively low curvature in almost all of the training images, which also tends to make the gradient in p steep here. If the organ is modeled as having a smooth low curvature surface near the bottom, and only a moderate variability in the location of the tangent point at the bottom edge of the bounding region, then the probability p would be expected to increase proportionally to the square root of the distance from the edge, resulting in an infinite gradient right at the edge, where p=0, in the general location where the organ is tangent to the edge for most of the training images. The gradient in p is also fairly great near the upper right edge of the atlas, but is not as great as it is near the center of the bottom edge, because the point where the organ is tangent to the right edge of the bounding region is not quite in this slice of the bounding region, for most of the training images, and the tangent point is even further from this slice, for the top and left edges. In addition, the gradient in probability is lower at the top and left edges, because the curvature of the organ is generally greater at the point where it is tangent to those edges of the bounding region, than for the bottom and right edges.

Near the point of steepest gradient in p, at the center of the bottom edge, the p=0 and p=0.1 contours are indistinguishable, both running along the bottom edge, and the p=0.2 contour is only 1 voxel above the bottom edge, which is 1% of the height and width of the bounding region. The p=1 contour 506 has its closest approach to the bottom edge at a distance of 13 voxels away, so the shortest distance between the p=0 and p=0.2 contours is less than 8% of the shortest distance between the p=0 and p=1 contours. This is typical of probabilistic atlases that are constructed in this way, for organs, such as the spleen, with relatively low surface curvature where they are tangent to the edge of their bounding region.

The appearance of the contours in FIG. 5A are different, where they are far from the edges of the bounding region. This may be seen, for example, near the lower right part of the atlas, and near the upper central part of the atlas, where the contours are oriented roughly at a 45 degree angle, going from lower left to upper right. In these regions, the gradient in probability is relatively low between the p=0.1 and p=0.2 contours, and is greater for intermediate values of p, between 0.2 and 0.8. The lower p regions represent a relatively small number of training images where the organ has an atypical shape, extending further to the lower right or further to the upper left than usual. In an atlas that is not based on aligning the bounding region of the organ in the different training images, but is based on a different method of aligning the training images, one might expect the contours at low p to behave in this way on all sides of the organ, because the bounding regions play no role in generating the atlas.

Segmenting Test Images

Figure 5B:
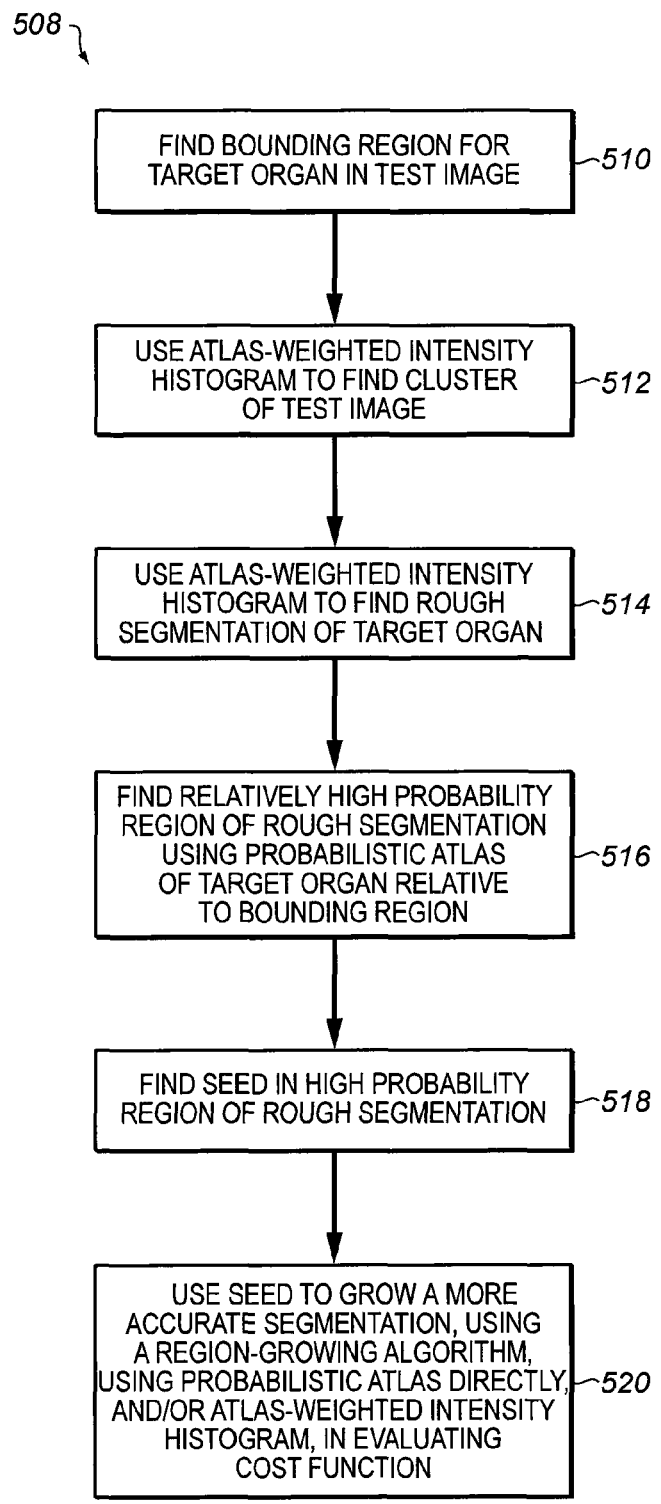
FIG. 5B is a flow chart showing how a probabilistic atlas of a target organ relative to a bounding region, such as that illustrated in FIG. 5A, may be used in segmenting the target organ, according to an exemplary embodiment of the invention.

FIG. 5B shows a flow chart 508 for segmenting a target organ in a test image, showing different ways in which a probabilistic atlas of the test organ relative to its bounding region, such as the probabilistic atlas illustrated in FIG. 5A, can be used to perform the segmentation, according to an exemplary embodiment of the invention. It should be understood that flow chart 508 includes several different procedures that each optionally make use of the probabilistic atlas in different ways, and the probabilistic atlas may be used in any one of the procedures, or any subset of the procedures, even it is not used for all of them.

At 510, a bounding region for the target organ is found in the medical image. Details on how this is done are described below, in flow chart 600 of FIG. 6. At 512, an atlas-weighted intensity histogram of the bounding region of the test image is optionally used to find a cluster that the test image belongs to. As described above, the training images are optionally grouped into clusters that correspond to different ways of using contrast agent, and the test image is assigned to one of the clusters. Optionally, the test image is assigned to a cluster by comparing an intensity histogram of the bounding region in the test image, weighted by the atlas probabilities obtained for the target organ in the training data, to the average or representative histograms for each of the different clusters in the training data, and finding for which cluster the average or representative histogram most closely matches the atlas-weighted histogram. This is the first example in flow chart 508 of a procedure in which the probabilistic atlas is optionally used. Further details of how the test image is assigned to a cluster are described below, at 608 and 610 of FIG. 6.

At 514, a rough segmentation of the target organ is found in the bounding region, by finding voxels that have a range of intensity expected for the target organ, and not expected for voxels that are near but outside the target organ, for example using the training histogram found at 220 in flowchart 200 of FIG. 2. Whether or not the training images are divided into clusters, an atlas-weighted intensity histogram of the bounding region of the test image is optionally used, in combination with the training histogram, to find the intensity values expected for voxels in the test image, and hence to find the rough segmentation for the target organ. This is the second example in flow chart 508 of a procedure in which the probabilistic atlas is optionally used. Further details of how the rough segmentation is found, using the atlas-weighted histogram of the test image and the training data, including making morphological improvements such as filling in holes, are described below, at 612-620 of FIG. 6.

At 516, once the rough segmentation is found, the probabilistic atlas is optionally used to find a relatively high probability region of the rough segmentation, for example the maximum probability region of the rough segmentation. This is the third example in flow chart 508 of a procedure in which the probabilistic atlas is optionally used. Finding the rough segmentation, and the high probability region of the rough segmentation, may be considered an attempt to find, at least approximately, a core region of the target organ that includes voxels that are especially typical of the target organ both in their location and in their intensity. As used herein, "core region" may refer to the high probability region of the rough segmentation, although this region may include a relatively small number of voxels that do not have intensities expected for the target organ, due to noise or due to small features within the organ, that were added to the rough segmentation by the morphological improvements.

At 518, a seed comprising one or more seed voxels is optionally found in the relatively high probability region of the rough segmentation. Details of how the high probability region is found, and how the seed is found, are given below in 622 of FIG. 6.

At 520, the seed found at 518 is used to grow a more accurate segmentation, using a region-growing algorithm. Optionally, the region-growing algorithm uses a cost function whose value depends on the probability values in the probabilistic atlas. This is the fourth example in flow chart 508 of a procedure in which the probabilistic atlas is optionally used. In addition, whether or not the cost function depends directly on the probability values in the probabilistic atlas, the cost function optionally depends on the atlas-weighted intensity histogram of the bounding region of the test image, as well as on the training histogram, for example as described below at 614 of FIG. 6. This is the fifth example in flow chart 508 of a procedure that optionally uses the probabilistic atlas. Details of how the more accurate segmentation is grown are given below in 624 of FIG. 6, and in FIGS. 8A and 8B.

FIG. 6 shows a flow chart 600 for a method of segmenting one or more target organs in a test image, according to an exemplary embodiment of the invention, using training data that was generated by the method of FIG. 2. The procedure starts at 602, when a test image is selected. At 604, the first target organ is selected for segmentation. Although FIG. 6 shows different target organs being segmented consecutively, in a loop going from 604 to 630, some or all of the different target organs are optionally segmented in parallel, instead.

The bounding region for the target organ is found at 606. Optionally, any known method is used for finding a preliminary segmentation for the target organ, and the bounding region is defined the same way as in the training images, for example as the smallest rectangular box, with principle axes aligned with the principle body axes, that includes all of the target organ according to the preliminary segmentation. Alternatively, a method is used that finds the bounding region of the organ in the image, even without first finding a preliminary segmentation of the organ. Known methods of finding a preliminary segmentation or a bounding region of a target organ in a medical image include:

1) Learning-based methods, based on knowledge encoded during an off-line training process, often involving manual or semi-manual ground-truth segmentations of training images, for example involving the locations of organs relative to a bounding box that may include the entire abdomen, or the entire body. Examples of such methods are described by Xiangrong Zhou, et al, "Automatic localization of solid organs on 3D CT images by a collaborative majority voting decision based on ensemble learning," *Computerized Medical Imaging and Graphics*, 36 (2012), 304-313, and by Antonio Criminisi, et al, "Regression forests for efficient anatomy detection and localization in computed tomography scans," *Med. Image Anal.* (2013), available from <http://dx.doi.org/10.1016/j.media.2013.01.001>.

2) Registration-based methods, in which a medical image is registered to an image in an atlas that covers a large field of view, such as the entire abdomen, or the entire body. An example of such a method is described in Hyunjin Park, et al, "Construction of an Abdominal Probabilistic Atlas and its Application in Segmentation," *IEEE Transactions on Medical Imaging*, Vol. 22, No. 4, April 2003, 483-492.

3) Any other known method of segmenting an organ in medical image, whose accuracy is insufficient, can be used to find a preliminary segmentation in order to find a bounding region in 606. For example, a method using neural networks and fuzzy rules for this purpose is described in Chien-Cheng Lee, et al, "Identifying multiple abdominal organs from CT image series using a multimodule contextual neural network and spatial fuzzy rules," *IEEE Transactions on Information Technology in Biomedicine*, Vol. 7, No. 3, September 2003, 208-217.

Alternatively, these or other known methods are adapted to give a bounding region for the target organ directly, without ever finding a preliminary segmentation of the target organ.

At 608 an intensity histogram is found for the voxels in the bounding region in the test image, with the contribution from each voxel weighted by a weighting factor that depends on the probability of the corresponding location in the probabilistic atlas. The location in the probabilistic atlas that corresponds to a given voxel in the test image is optionally defined, for example, by a linear mapping from the bounding region in the test image to the probabilistic atlas, with possibly different scaling factors in each principal direction, and the probability of the location is optionally found from the probabilities of the voxels in the probabilistic atlas by any known interpolation scheme, for example using the probability of the nearest voxel in the atlas. For example, the weighting factor is the probability, or is proportional to the probability. Alternatively, the weighting factor is a nonlinear function of the probability, for example a function proportional to the square of the probability, or another power of the probability. Optionally the weighting function is an increasing function of the probability, so that voxels with greater probability of belonging to the target organ are given greater weight. Optionally, the distribution of probability in the probabilistic atlas is smoothed or otherwise processed, before using it to find the weighting factor. The resulting test histogram represents the distribution of voxel intensities in the organ and its vicinity. Optionally, the test image is smoothed slightly before calculating the test histogram, although the inventors have found that better results are generally obtained without smoothing. If the training images are smoothed before calculating the training histogram, then optionally the test image is smoothed in the same way, before calculating the test histogram. Optionally, the range and bin size of intensities for the test histogram is the same as the range and bin size of intensities for the training histogram, for example, in the case of CT images, a range of −990 to +1000 HU, with a bin size of 5 HU has been found by the inventors to work well. Optionally, the test histogram is normalized to its peak value, so that it can have values ranging between 0 and 1.

In some embodiments of the invention, instead of finding the full test histogram at 608, only some characteristics of the weighted distribution of voxel intensities in the bounding region of the test image are found. For example, optionally the peak value and width of local peaks in the weighted distribution of voxel intensities are found directly from the intensity values of the voxels, without ever finding the full test histogram. For example, the weighted number of voxels is found within each of a several relatively coarse bins of intensity, and within each bin that has a great enough weighted number of voxels, the weighted mean and standard deviation of intensity is found. In this case, the information on the height and width of local peaks is used instead of the full test histogram, in what follows.

At 610, if the training data includes separate training histograms for different clusters of training images having different contrast characteristics, the test histogram found in 608, or other information about the weighted distribution of voxel intensities in the bounding region, such as mean value or standard deviation, is optionally used to assign the test image, for purposes of segmenting this target organ, to a cluster that has contrast characteristics similar to those of the target organ in the test image. Alternatively a different kind of test histogram is used, for example an unweighted intensity histogram of the bounding region in the test image. The test image is assigned to a cluster, for example, by comparing the test histogram to the average or representative intensity histogram found for each cluster, as described above at 214 of FIG. 2, and determining for which cluster the average or representative intensity histogram is closest to the test histogram, optionally using the same distance measure used at 214 in FIG. 2 for sorting the training images into clusters, for example, the Bhattacharyya distance, as a measure of distance between the histograms, or using any other distance measure. The test image is then assigned to that cluster. Optionally, the test histograms and the average or representative histograms of the clusters are defined in a way that they would be expected to be similar, if the test image has similar contrast characteristics to the training images of a cluster. For example, if the test histogram is an unweighted histogram of the bounding region of the test image, then the average or representative histogram of a cluster is optionally based on intensity histograms of the entire bounding region. While if the test histogram is an atlas-weighted histogram of the bounding region of the test image, then the average or representative histogram of a cluster is optionally based on inside histograms, or on a combination of inside histograms and histograms of the entire bounding region. In this way, the test image, for purposes of segmenting this target organ, will be assigned to a cluster of training images for which the distribution of intensities within the organ and its vicinity is similar to the distribution of intensities in the bounding region found for the target organ in the test image. The training data for that cluster may then provide useful information on the expected distribution of intensities and gradients of the test organ, and its background voxels, in the test image.

If the training data does not include multiple clusters, at least for this organ, then in effect there is only one cluster for this organ, and there is no need to assign the test image to a cluster, for purposes of segmenting this organ.

At 612, the training histogram for this cluster and target organ is read into the computer performing the segmentation. At 614, the training histogram is multiplied by the test histogram found in 608, for the different values of voxel intensity, and optionally normalized to the height of its highest peak, to find a posterior probability histogram. The posterior probability histogram is a histogram of the intensities in the bounding region found for the target organ in the test image, but with an enhancement of peaks at values of intensity that are usually associated with voxels in the target organ, and with a suppression of peaks at values of intensity that are usually associated with voxels that are in the bounding region of the target organ but outside the target organ itself.

Figure 7A:
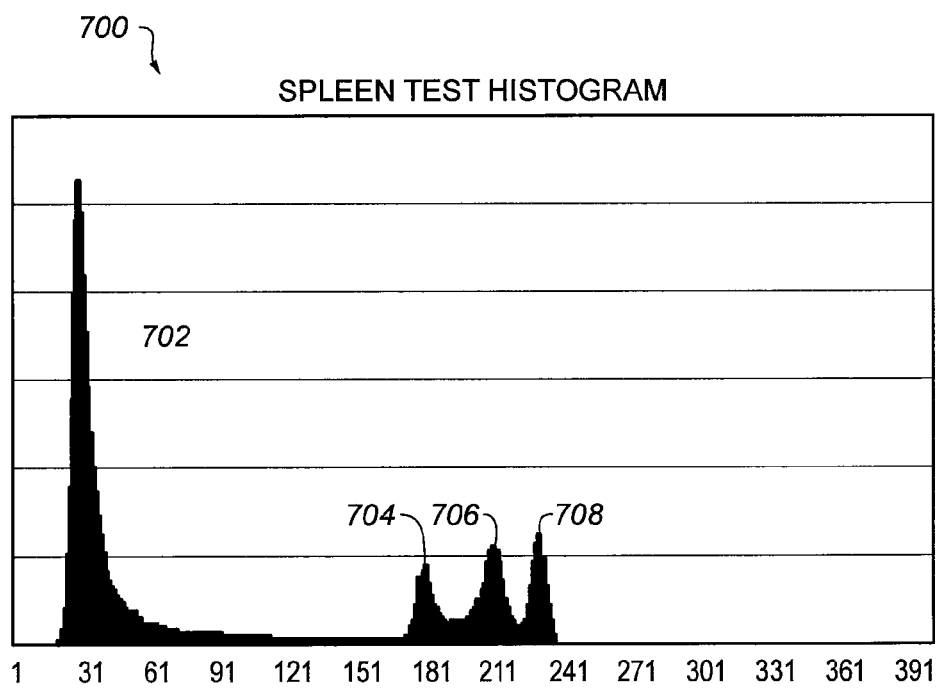
FIGS. 7A and 7B show examples of weighted test histograms obtained from a medical image segmented according to the method of FIG. 6.
Figure 7B:
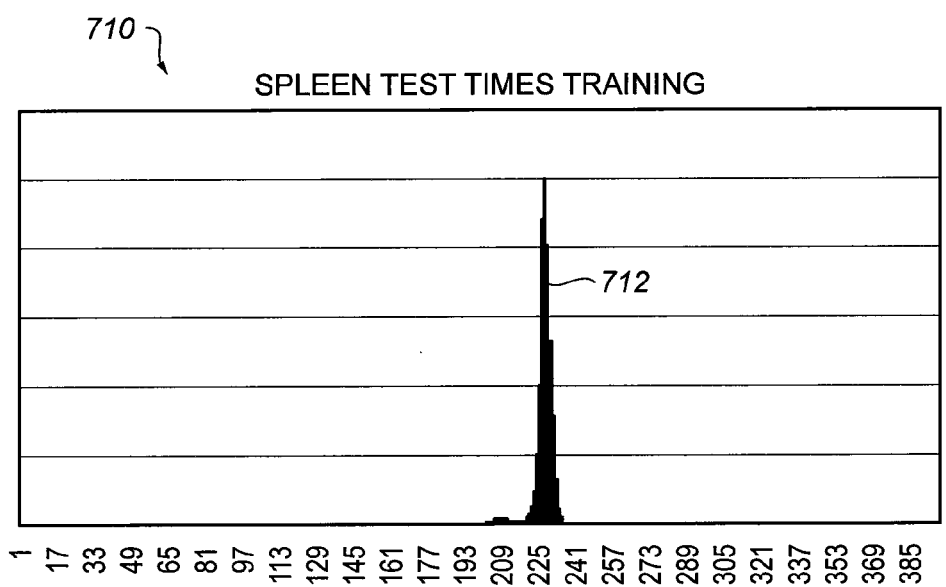

Reference is now made to FIGS. 7A-7B where there is shown a plot 700 of a test histogram for the spleen, found for a test image, using the method described above for 608 in FIG. 6. As in the training histogram shown in FIG. 3, in plot 700 the horizontal axis shows the bin number for the intensity values, which range from −990 HU to +1000 HU, each bin being 5 HU wide. The scale of the vertical axis is arbitrary. There are four peaks in the test histogram, labeled 702, 704, 706, and 708. Although the data that went into the histogram was weighted by the probability of the voxel being inside the spleen, based on the probabilistic atlas illustrated in FIG. 5, there is some variation in the location of the boundaries of the spleen in different images, so the test histogram in FIG. 7A has some contributions from voxels in the vicinity of the spleen but outside the spleen. The four peaks in histogram 700 likely represent different organs or regions of organs each with fairly uniform intensity, including the spleen and other organs near the spleen. Multiplying the test histogram in plot 700 by the training histogram for the spleen, shown in FIG. 3, provides a posterior probability histogram, shown in a plot 710 in FIG. 7B, which picks out which peak in plot 700 is due to the spleen. Plot 710 has a single dominant peak 712, corresponding to peak 708 in plot 700, and this peak represents voxels that are in the spleen, possibly only voxels in a uniform central part of the spleen. The other peaks in plot 700 apparently represent other organs and regions near the spleen. For example, peak 702 appears to represent the abdominal cavity. Peaks 704 and 706 may represent other organs adjacent to the spleen, or inhomogeneities within the spleen or adjacent organs, such as cysts, tumors, or blood vessels. Peak 706 appears to represent the liver, part of which is in the bounding region of the spleen. Peaks corresponding to 702 and 704 do not appear in plot 710, and a peak corresponding to 706 appears only at very low amplitude, because the training histogram has very low amplitude for intensity values that are largely found outside the spleen within the spleen bounding region. Optionally, the posterior probability histogram is normalized by dividing it by its peak value, so that it ranges from 0 to 1, which will be useful later.

At 616, the intensity value at the highest point of the posterior probability histogram, the top of peak 712 in FIG. 7B, is found, as well as a measure of the width of the peak around the highest point, for example the standard deviation of the peak, or its full width at half maximum. At 618, a mask is created, within the bounding region of the target organ in this image, of voxels with intensities within a range predicted as likely for the target organ, for example within half a standard deviation of the peak of the posterior probability histogram, or within the width of the peak at half maximum. Optionally, the mask is based on a slightly smoothed version of the image, even if the training and test histograms are based on unsmoothed images. Using a slightly smoothed image for creating the mask at 618 has the potential advantage that the mask will be less likely to include isolated voxels from nearby organs, which, due to noise, have an intensity value that is typical of the target organ, instead of an intensity value typical of the organ that they belong to. It should be understood that the method used for creating the mask at 618 is not necessarily intended to produce a mask that covers the entire target organ, even approximately, but rather is intended to produce a mask that covers at least a core region of the organ, and excludes voxels that do not belong to the organ. In a case where the organ includes two regions with very different intensities, such as the inner and outer parts of the kidney which may have very different intensities when contrast agent is used, it is especially likely that the mask created at 618 will not cover the entire organ, but only a core region of the organ.

At 620, the mask generated in 618 is optionally morphologically improved, for example filling in holes in its interior that are completely surrounded by mask voxels, or filling in holes that are completely surrounded by mask voxels within a slice at a particular orientation, for example within an axial slice, or that are completely surrounded by mask voxels within a slice in any principal orientation (axial, coronal, or sagittal), or that are completely surrounded by mask voxels within a slice in either of two principal orientations, or in any two principal orientations, or in all three principal orientations. Such holes may result from noise in the image, as well as from small blood vessels, liver bile ducts, or other small features inside the target organ, that have a different intensity than most of the voxels of the target organ but are still considered part of the target organ. An example of a specific procedure for morphologically improving the mask, which the inventors have found gives good results at least for abdominal organs is as follows: 1) The mask is morphologically closed by 2 mm, to include small interior islands of different intensity value, perhaps due to noise. "Morphologically closing by 2 mm" means dilating by 2 mm, and then eroding by 2 mm. 2) Morphologically opening the mask by 5 mm, to disconnect nearby organs. "Morphologically opening by 5 mm" means eroding by 5 mm, and then dilating by 5 mm. However, if the morphological opening deletes the entire mask, then it is undone. 3) Deleting any components that are smaller than 4000 cubic millimeters in volume, but only if there is a remaining component that is more than 4000 cubic millimeters in volume. 4) Filling in any cavities that are completely surrounded by mask voxels in their axial slice. This adds to the mask some blood vessels, liver bile ducts, lesions, cysts, and low intensity regions in the middle of kidneys whose outer regions have much higher intensity when contrast agent is used. The resulting mask, after the morphological improvements, may be considered a rough segmentation of the target organ, in this image.

At 622, a seed voxel is found for segmenting the organ, by looking at the part of the rough segmentation found at 620, which is based only on voxel intensities, that has the maximum probability value in the probabilistic atlas, which is based on voxel location, or by looking at a part of the rough segmentation that has relatively high probability values in the probabilistic atlas. In all the cases tested by the inventors, the maximum probability region of the rough segmentation has always had a probability of 100%, but this is not a necessary condition for the method to work. The maximum probability region, or high probability region, of the rough segmentation gives a set of voxels that are extremely likely to be within the target organ, based both on the intensity and the location of the voxels, and are thus useful to use as seeds for segmenting the organ using a region-growing algorithm. Although the rough segmentation alone is optionally used to find the seed voxel, using the maximum probability region of the rough segmentation has been found by the inventors to give better results, because it usually prevents a situation where the seed voxel is in a nearby organ, that extends into the bounding region of the target organ, and has similar intensity values to the target organ. Such a nearby organ is likely to be in a part of the bounding region for the target organ that has low probability in the probabilistic atlas, so can often be excluded by taking into account the information in the probabilistic atlas.

Optionally, the seed is a voxel that corresponds to the location most likely to fall within the target organ found at 230 of FIG. 2, and mapped from the probabilistic atlas to the bounding region of the target organ in this image. If the voxel is outside the rough segmentation, then optionally a voxel nearest to that voxel, within the rough segmentation, is chosen as the seed. Alternatively, the seed is a voxel furthest from the boundary of the maximum probability region of the rough segmentation. Alternatively, the seed is a voxel furthest from the boundary of the rough segmentation, that falls within the maximum probability region of the rough segmentation. The inventors have found that using a voxel furthest from the boundary of the maximum probability region of the rough segmentation often gives the best results of all these alternatives, since such a voxel is deep within both the rough segmentation, and the maximum probability region.

Optionally, instead of mapping the probabilities from the probabilistic atlas to the bounding region in the test image, and finding the seed voxel in the coordinates of the test image, the rough segmentation is mapped from the bounding region in the test image to the coordinates of the probabilistic atlas, the seed voxel is found in those coordinates, and is then mapped back to the coordinates of the test image. Although the two procedures are mathematically equivalent, working in the coordinates of the probabilistic atlas may be more computationally efficient. The following algorithm is an example of such a computationally efficient procedure for finding the seed: 1) an empty mask, called the "intersection mask" is created, with dimensions, in voxels, corresponding to the dimensions of the probabilistic atlas. 2) Look at each voxel in the probabilistic atlas, and find the closest voxel to its mapped location in the bounding region of the test image. If the closest voxel in the bounding region of the test image falls within the rough segmentation, and if the probability value of that voxel in the probabilistic atlas is at least as great as that of any voxel that has been included in the intersection mask so far, then add that voxel to the intersection mask, and update the highest probability value for any voxel included in the intersection mask so far, to the probability value for that voxel. 3) After doing this for each voxel in the probabilistic atlas, look again at each voxel in the intersection mask, and exclude from the intersection mask any voxel that has a probability value less than the maximum probability value of all voxels included in the intersection mask. 4) The voxel furthest from the boundary of the intersection mask is selected, the distance optionally defined not as the Euclidean distance in the space of the probability atlas, but as the Euclidean distance in the test image, taking into account the linear mapping of the probability atlas to the bounding region in the test image. 5) The closest voxel in the test image, to the location of the selected voxel in the intersection mask mapped into the test image, is designated as the seed voxel. It is noted that this procedure will work even in the extreme case there the maximum probability value for any voxel in the rough segmentation is zero, in which case the seed voxel will be the voxel furthest from the boundary of the rough segmentation, but in practice, the maximum probability value of all voxels in the intersection mask is expected to be close to 100%. Optionally, if the maximum probability value is below some threshold, such as 90% or 80% or 50%, then the algorithm ends and generates a failure message, since in this case it is likely that either the bounding region or the training histogram for the target organ is completely wrong.

At 624, the seed voxel found in 622 is used to grow a more accurate segmentation of the target organ, using a region-growing algorithm, for example a fast-marching algorithm. Further details of the region-growing algorithm are given below in the description of FIG. 8A.

At 626, one or more morphological filling operations are optionally performed on the more accurate segmentation found at 624. Optionally, the morphological filling operations include any of the filling operations described as optionally being performed at 620, for example adding to the segmentation all voxels that are entirely surrounded, in a slice in a particular orientation, for example an axial slice, by voxels that are already included in the segmentation. Such fill operations can add to the segmentation some blood vessels, bile ducts when the target organ is the liver, and low intensity regions in the interior of the organ when the target organ is a kidney, especially when contrast agent increases the intensity in an outer region of the kidney, but has less effect deeper in the interior of the kidney. Optionally, when the target organ is a kidney, voxels are added to the segmentation when they are entirely surrounded by voxels already in the kidney, in their coronal or sagittal slice, provided the intensity of the voxel has a posterior probability histogram value greater than a critical value, for example greater than 0.01, where, as described above, the posterior probability histogram has been normalized to its peak value. This procedure has been found to be effective at adding to the segmentation voxels deep in the interior of the kidney where contrast agent has not enhanced the intensity as much as in an outer portion of the kidney, while not adding to the segmentation voxels that are located outside the kidney, in the hollow of the kidney.

At 628, any leaks of the segmentation into nearby organs or other structures are optionally morphologically fixed, for example using a procedure that is described below in FIG. 9.

At 630, if there are more target organs to be segmented, then the next target organ is looked at, at 604. If all of the target organs have been segmented, then, at 632, any overlap regions between two segmented target organs are optionally found. Optionally, only pairs of target organs that are known to be commonly adjacent to each other, and/or have similar enough intensity distributions, are examined to see if their segmentations overlap, for example the spleen and the left kidney, the liver and the right kidney, or the liver and the spleen. Alternatively every pair of target organs is checked for overlap regions. The voxels in each of the overlap regions are then optionally assigned to one of the overlapping target organs, at 634, for example using a method described below in FIG. 10, and in some cases even voxels that are not in overlap regions are reassigned to different organs, or are removed from the organ they are assigned to without assigning them to a different organ, as described in FIG. 10. Optionally, overlap regions are assigned to only one of the target organs, only if the overlap region is at least a minimum size, for example at least 100 cubic millimeters.

At 636, any region of a segmented organ, generally a small region, that has become disconnected from its seed, as a result of the reassignment of voxels in 634, is optionally removed from the segmentation of the organ. But optionally this is not done if it would result in removing too large a fraction of the voxels in the segmentation of the organ, in particular if the seed no longer lies within the segmentation so that all voxels in the segmentation are disconnected from the seed. Optionally, removing disconnected regions for all target organs is done only after overlap voxels between all pairs of target organs have been found and assigned at 632 and 634. Alternatively, after overlap voxels for a given pair of target organs have been assigned, any resulting disconnected regions for those two target organs are removed, before finding and assigning overlap voxels for the next pair of target organs. At 638, any leaks of the segmentation of any organ into nearby organs or other structures, that may have appeared as a result of reassigning voxels in 634, are optionally morphologically fixed, for example using the same procedure as in 628.

At 640, a decision is optionally made whether to segment the target organs over again, in a new iteration, starting again at 604, using the present segmentation of target organs to find an improved bounding region for each target organ at 606. Optionally, a new iteration is always made after the first iteration, and iterations are repeated until a stopping criterion is reached, based for example on stopping the iterations when the difference in the segmentations between the last two iterations falls below a threshold, and/or stopping the iterations when the number of iterations has exceeded a maximum number. Performing more iterations can potentially produce a more accurate segmentation, since a more accurate bounding region may result in a more accurate intensity histograms and more accurate probabilities derived from the probabilistic atlas, which can lead to more accurate segmentations. Optionally, the bounding region of a target organ for the new iteration is defined as the smallest rectangular box, aligned with the principal axes, that includes all of the voxels of the target organ found in the segmentation in the previous iteration. Alternatively, the bounding region of a target organ for the next iteration as the smallest rectangular box that in some sense includes almost all of the voxels of target organ found in the segmentation in the previous iteration. For example, the bounding region is defined as a rectangular box, which extends, in each principal direction, from the $5^{th}$ percentile to the $95^{th}$ percentile of values of the coordinate for that principal direction for any voxels in the segmentation found in the previous iteration. Defining the bounding region in such a way may avoid outliers in the spatial distribution of voxels in the segmentation, that may result from any minor leaks that occurred during the segmentation procedure and were not properly fixed.

Alternatively, only a single iteration of the segmentation procedure is performed. The inventors have found that, for some applications of the method, the improved accuracy of segmentation that may result from using more than one iteration does not justify the increased computer time needed.

When no further iterations are to be done, the segmentation procedure ends at 642.

Region-Growing Algorithm

Figure 8A:
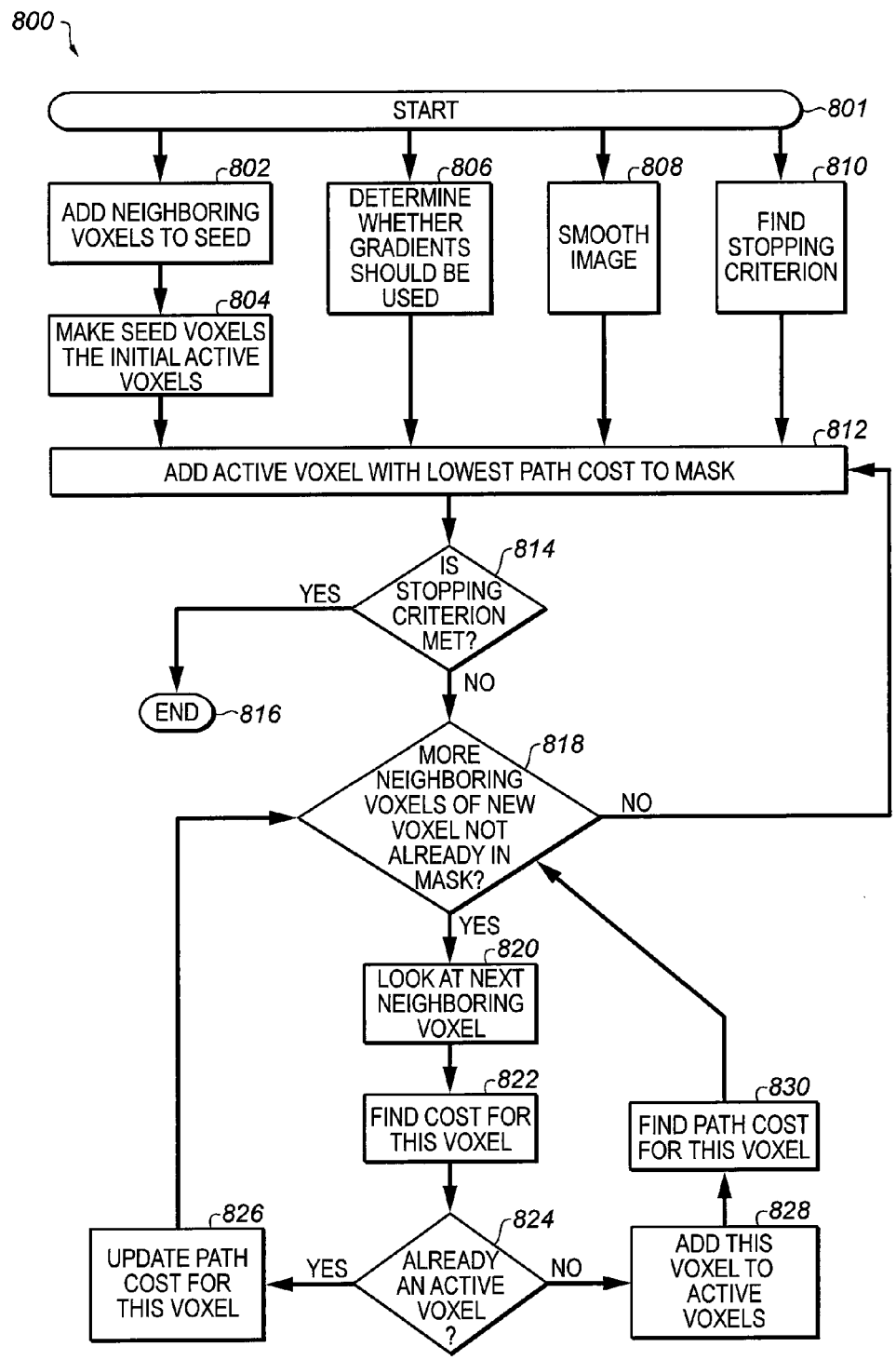
FIG. 8A is a flow chart, showing further details of growing a more accurate segmentation of the target organ according to the method of FIG. 6.

FIG. 8A shows a flow chart 800, for a method of growing a more accurate segmentation of the target organ in a test image, using a region-growing algorithm, that is optionally used at 624 of FIG. 6. Region-growing algorithms are described by J. A. Sethian, *Level Set Methods and Fast Marching Methods: Evolving Interfaces in Computational Geometry, Fluid Mechanics, Computer Vision, and Materials Science* (Cambridge University Press, 1996). In a region-growing algorithm, such as a fast-marching algorithm or a Dijkstra algorithm, one or more seed voxels are initially assigned to a mask. The mask expands by adding to it active voxels, which are neighboring voxels to the voxels already in the mask, until a stopping criterion from a set of one or more predefined stopping criteria is reached. Each active voxel is assigned a cost function, which optionally is a local function of the voxel, depending for example on its intensity and position. From this cost function, a path cost is computed for the voxel, defined as the cost function integrated along the path of expansion from the one or more seed voxels to that voxel. The fast-marching and Dijkstra algorithms differ in how they define the path between voxels and hence the path cost, with the fast-marching algorithm allowing the path to be oriented obliquely with respect to the arrangement of voxels. The active voxels are ordered in order of ascending path cost, and at each iteration the active voxel with the lowest path cost is added to the mask. The stopping criterion is optionally based on the path cost. For example, the stopping criterion is optionally that the path cost for the voxel currently being added to the mask exceeds some maximum value, which means that all other active voxels have path cost at least that high.

In the method of flow chart 800, a probabilistic atlas as described for example at 228 in FIG. 2, and included in the training data, is used to evaluate the cost function at the voxels encountered by the growing segmentation mask. Unlike standard fast-marching algorithms, for which the cost function is a local function of each voxel, in the method of flow chart 800 the cost function optionally also depends on the volume to which the mask has grown so far.

The process for flow chart 800 starts at 801. Before beginning the fast-marching algorithm, four preliminary actions are optionally taken: 802 followed by 804, 806, 808, and 810. These actions are optionally taken in parallel as shown in FIG. 8A, or consecutively in any order, or some are performed in parallel and some consecutively. If performed consecutively, any of 806, 808 and 810 are optionally performed between 802 and 804.

At 802, one or more voxels are optionally added to the seed. For example, the four voxels that are adjacent to the seed voxel, in the axial slice of the seed voxel, are added to the seed voxel, and the region-growing algorithm begins from the additional voxels as well as from the original seed voxel. Enlarging the seed voxel in this way has the potential advantage of making the region-growing algorithm insensitive to the presence of noise which significantly changes the intensity of the seed voxel, so that it is outside the range of intensity expected for the test organ. If the seed is enlarged, so that it also includes a few other voxels at least one of which is not very affected by the noise, then the integrated cost function along a path from the seed to other voxels will not be substantially affected by the noise. This is potentially important when assigning voxels in an overlap region to one of the overlapping target organs, as will be described below in FIG. 10, since the path cost plays a role in deciding which target organ an overlap voxel should be assigned to.

At 804, the seed voxels, including any neighboring voxels added to the seed at 802, are made the initial active voxels for the fast marching algorithm, and nominally assigned a path cost of zero.

At 806, a determination is optionally made whether or not the cost function, used in the region-growing algorithm, will depend on the local gradient of intensity. The gradient is optionally used if the gradients expected for the boundary voxels according to the training data, as shown for example in FIG. 4, are sufficiently separated from the gradients expected for interior voxels according to the training data, for this organ. For example, optionally gradients are used if and only if the median gradient of boundary voxels is greater than the median gradient of interior voxels, plus 1.5 times the standard deviation gradient for interior voxels, for this target organ. The inventors have found that, in the tests done with segmenting abdominal organs, with various contrast characteristics, in the great majority of cases this condition was met, and gradients were included in the cost function.

Optionally, at 808, the test image is slightly smoothed. For example, the intensity of each voxel is set equal to an average, possibly a weighted average, of the original intensity of the voxel and the intensity of its nearest neighbors, in three dimensions or only within a slice, for example within an axial slice. Such smoothing has the potential advantage that it may reduce noise which may cause voxels inside the target organ to have intensities that are not in the expected range for the target organ, but optionally the test image is not smoothed so much that the boundaries of the target organ are significantly blurred. Optionally, the smoothing uses anisotropic diffusion, which is greatest in directions perpendicular to the direction of the intensity gradient, to avoid blurring of the boundaries while still reducing noise. Optionally the image is not smoothed at all.

At 810, a stopping criterion is found, for example a threshold value that the path cost of the voxel currently being added to the mask has to exceed, in order to stop expansion. Appropriate values of the path cost for the stopping criterion depend on how the cost of a voxel is defined, and exemplary choices for the stopping criterion will be discussed below, in the description of 814, and examples are given of a cost function, in the description of FIG. 8B. Optionally, the threshold value is chosen to be at least a few times higher than the path cost for most of the voxels, or almost all of the voxels, in the high probability region or maximum probability region of the rough segmentation optionally found at 622 of FIG. 6, for example at least 3 times higher, or at least 5 times higher, or at least 10 times higher. However, there may be a few voxels in this core region that have much higher path cost, because they are in small islands of atypical image intensity that were added to the rough segmentation by morphological improvements at 620 of FIG. 6, or because they are located in small islands of high probability and expected image intensity for the target organ, that are disconnected from the bulk of the core region. Those few atypical voxels may not have much lower path cost than the threshold value, and might even have higher path cost than the threshold value, even if a majority or great majority of voxels in the core region have much lower path cost than the threshold value.

Alternative or additional stopping criteria are also optionally used, for example the procedure optionally stops once a maximum total number of voxels has been added to the mask.

At 812, the active voxel with the lowest path cost is added to the mask. If two or more active voxels share the lowest path cost, as will be true initially if there is more than one seed voxel with a path cost of zero, then one of them is chosen to add to the mask at this time.

At 814 a decision is made whether the stopping criterion is satisfied. The stopping criterion is optionally that the path cost for the voxel that was added to the mask at 812 is greater than a threshold, which means that the path cost is greater than the threshold for all active voxels. The threshold of the path cost for stopping is optionally set to be proportional to the cube root of the mean volume V expected for the target organ, from the training data. If the target organ were spherical, with volume V, then its radius would be $(3V/4\pi)^{1/3}$. The inventors have found that a threshold that works well, for the path cost, is $10(3V/4\pi)^{1/3}$, in the case where the gradient cost is used as part of the cost function, and with the cost function calculated as described below at the end of the description of FIG. 8B. In the case where the gradient cost is not used as part of the cost function, because the boundary voxels are not clearly distinguished from the interior voxels by their higher intensity gradient, a lower threshold is optionally used for the path cost, for example $1.5(3V/4\pi)^{1/3}$, still with the same definition of cost function. It is potentially advantageous to use a lower threshold in this case, because an increase in intensity gradient will not stop the expansion at the boundary of the target organ, so it may be important to use a lower threshold for path cost, in order to stop the expansion before it leaks into a neighboring organ.

Optionally, an additional stopping condition is that there are no more active voxels. This would occur, for example, if the threshold were set so high that all of the voxels in the image are added to the mask, before any voxel has a path cost greater than the threshold. In practice, assuming that the test image does not consist entirely of voxels in the target organ, a lower threshold should be chosen, in order to obtain an accurate segmentation of the target organ, and the stopping condition would be met when there are still active voxels.

If the stopping criterion is satisfied, then no more voxels are added to the mask, and the fast marching algorithm ends at 816.

If the stopping criterion is not satisfied, then at 818, it is determined whether there are neighboring voxels to the new voxel added to the mask, that are not already in the mask and have not yet been considered. If there are no such neighboring voxels, then the next active voxel with the lowest path cost is added to the mask at 812. If there are such neighboring voxels, then one of those neighboring voxels is considered at 820. First, at 822, the cost function is evaluated for that voxel. Details of how the cost function is evaluated, and how it optionally makes use of the probabilistic atlas, are given below in FIG. 8B. In standard fast marching, it is not necessary to evaluate the cost function if the voxel is already an active voxel, which would have had its cost function evaluated before, but only if it is to be newly added to the active voxels, because the cost function depends only on local properties of the voxel and does not change as the fast marching proceeds. However, in the fast marching algorithm described by flow chart 800, the cost function depends on the volume that the mask has reached so far, so the cost function may have changed even if it was evaluated previously. At 824, it is determined if that neighboring voxel is already an active voxel. If it is, then at 826, its path cost is updated. This is done by finding a tentative new path cost for it. In the case where the region-growing algorithm is a fast-marching algorithm, the tentative new path cost is found by solving an Eikonal equation, using the cost function of the voxel together with the path costs of all of its neighboring voxels that are already in the mask. A somewhat different definition of path cost is used for other region-growing algorithms, such as the Dijkstra algorithm. Further details on how the new path cost is calculated in the fast-marching algorithm and in related algorithms are provided on pages 86-100 of the book by Sethian referenced above. If the new path cost is lower than the old path cost of the neighboring voxel, then its path cost is lowered to the new value. If the old path cost is lower, then that value is kept. In this way, each active voxel always has the lowest path cost for any path connecting it to the seed, that has been explored so far.

If the neighboring voxel being considered is not already an active voxel, then it is made an active voxel at 828. The path cost is found at 830, by solving an Eikonal equation, using the cost function of the voxel together with the path costs of all of its neighboring voxels that are already in the mask, in the case where the region-growing algorithm is a fast-marching algorithm. Optionally, the active voxels are stored in the computer memory in a heap that is sorted by path cost, so that the active voxel with lowest path cost can be easily found at 812, each time a voxel is to be added to the mask. In this case, the location of an active voxel in the heap is adjusted or initially determined after the path cost is found at 826 or 830.

After the path cost has been found for this neighboring voxel at 830, or updated at 826, a decision is again made at 818 whether there are any more neighboring voxels, to the new voxel added to the mask, that are not already in the mask and have not yet been considered.

Figure 8B:
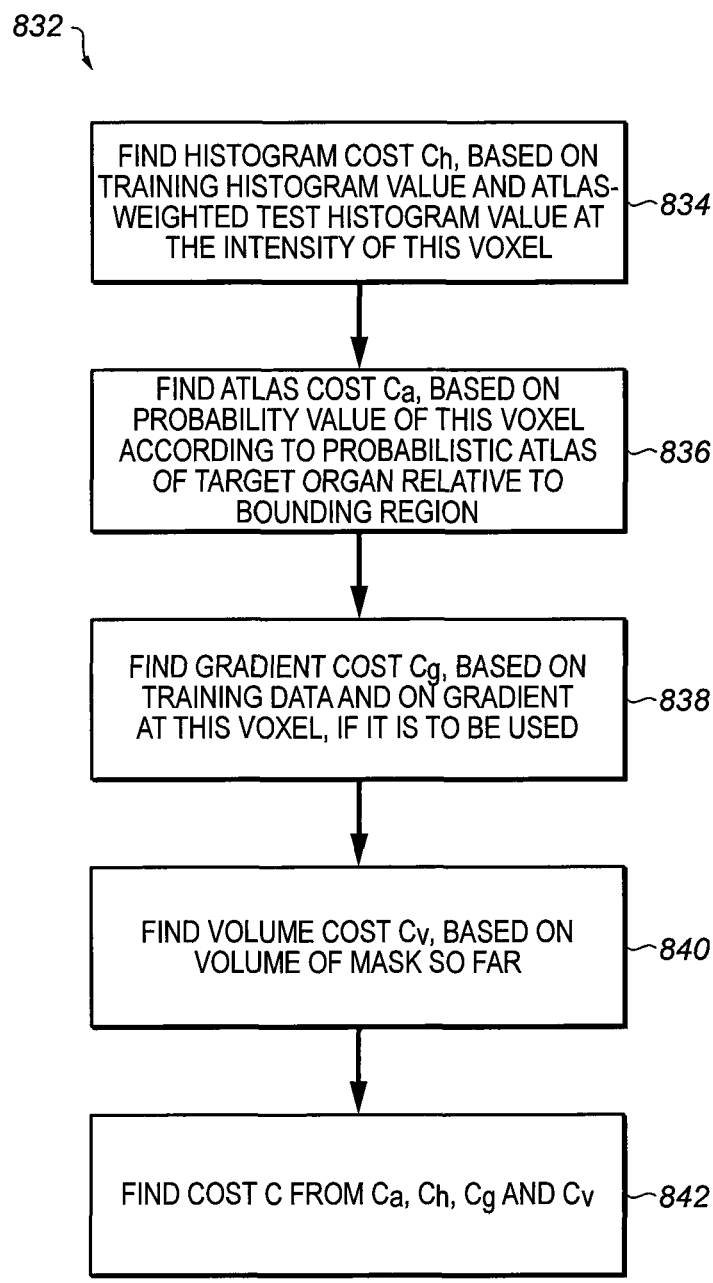
FIG. 8B is a flow chart, showing further details of finding the cost of a voxel according to the method of FIG. 8A.

FIG. 8B shows a flow chart 832 with further details of how the cost function of a voxel is evaluated at 822 of FIG. 8A. The cost function for each voxel optionally depends on one or more of the intensity of the voxel (histogram cost), the location of the voxel relative to the bounding region (atlas cost), the intensity gradient of the voxel (gradient cost), and total volume of the mask so far (volume cost). It should be understood that the intensity and intensity gradient refer to the smoothed image, if the image has been smoothed at 808.

The histogram cost $C_h$ is evaluated at 834, and is lower, for example, for voxels which have intensity values for which the posterior probability histogram is relatively high, than for voxels with intensity values for which the posterior probability histogram is relatively low. The probabilistic atlas optionally plays a role in evaluating the histogram cost, because the posterior probability histogram depends on the test histogram, which may be weighted according to the probabilistic atlas.

The atlas cost $C_a$ is evaluated at 836, and is lower, for example, for voxels for which the probability for the corresponding voxel in the probabilistic atlas is relatively high, than for voxels for which the corresponding voxel in the probabilistic atlas is relatively low.

The gradient cost $C_g$ is evaluated at 838, and is lower, for example, for voxels for which the intensity gradient is in a range expected for voxels in the interior of the organ, than for voxels for which the intensity gradient is much greater than expected for voxels in the interior. As noted above, the cost optionally does not depend on the intensity gradient at all if the ranges expected for voxels in the interior and at the boundary are too similar to each other, and in this case, the gradient cost is optionally not evaluated at all.

The volume cost $C_v$ is evaluated at 840, and is lower, for example, for any voxel, if the volume of the mask so far is much less than the expected volume for the target organ, than if the volume of the mask so far is comparable to the expected volume, and the cost is optionally even higher if the volume of the mask so far is greater than the expected volume.

At 842, the cost C of the voxel is found in terms of the histogram cost, the atlas cost, the gradient cost in some circumstances, and the volume cost.

Optionally, the voxels in a high probability core region of the target organ all have very low or zero cost. This has the potential advantage that all the voxels in the core region will be added to the mask with the path cost still well below the value required for the stopping criterion, and as a result, the set of voxels included in the final mask, when the expansion is finished everywhere, will be insensitive to the exact location of the seed. It also has the potential advantage that, when overlap voxels between two organs are assigned to one of the organs, as described below in FIG. 10, based on their path cost for each of the organs, any voxel in the core region of the first organ and not in the core region of the second organ will have lower path cost for the first organ, even if the first organ is much larger in size than the second organ. For example, the cost function and stopping criterion are optionally defined so that a high probability core region covers at least 50% of the volume of the organ, or at least 75% of the volume, or at least 90% of the volume, with the core region defined as the voxels for which the path cost is no more than 5%, or no more than 10%, or no more than 20%, or no more than 30%, or no more than 50%, of the value of the path cost required for the stopping criterion.

The following procedure for finding the cost function of a voxel has been found by the inventors to be suitable for some organs in the abdomen:

The histogram cost $C_h$ depends on the value of the posterior probability histogram at the intensity value of the voxel, in the original or smoothed image. If the value of the histogram, normalized to its peak value, is less than 0.0001, and at least 8 voxels have been added to the segmentation mask so far, then $C_h$ is set to be infinite, and hence the cost function is infinite, thus preventing the segmentation from entering such unlikely voxels. If fewer than 8 voxels have been added to the mask so far, however, an infinite cost function is not set for this voxel, to avoid having the segmentation end almost at the beginning, in case the seed happened to fall on a noisy patch of the image. Instead, the segmentation is given a chance to grow past this noisy patch into a less noisy region. For histogram value greater than 0.0001, or near the very beginning of the fast marching, $C_h$ is set equal to a positive power of the inverse of the posterior probability histogram value at the intensity value of the voxel, for example the square of the inverse of the posterior probability histogram value. This results in the cost rising rapidly as the intensity moves to values that are relatively more likely to be found outside the target organ, within the bounding region, and relatively less likely to be found in the target organ. In some embodiments of the invention, $C_h$ rises even more rapidly, for example like the fourth power of the inverse of the posterior probability histogram value, for subsequent iterations of the method shown in flow chart 600, with the bounding region revised according to the segmentation of the target organ found in the previous iteration. This is potentially advantageous, because the bounding region may be known more accurately in subsequent iterations, so the weighting according to the probabilistic atlas, which is used in finding the test histogram at 608 in FIG. 6, may be more accurate in subsequent iterations, and the resulting posterior probability histogram may be more reliable. Alternatively, $C_h$ is defined in the same way for subsequent iterations as for the first iteration, which has the potential advantage that inhomogeneities in intensity inside the target organ, for example due to blood vessels or lesions, will not be further penalized in subsequent iterations.

The atlas cost $C_a$ depends on whether the voxel is inside the bounding region, and if it is, it depends on the atlas probability of the voxel, which is defined as the probability of the nearest voxel in the probabilistic atlas to the location to which the voxel maps, using the linear mapping that maps the bounding region to the probabilistic atlas. In the first iteration of the procedure of flow chart 600, for voxels inside the bounding region, $C_a$ is set to −1 times the atlas probability. In the first iteration, for voxels outside the bounding region, $C_a$ is set to 0.2 times the Euclidean distance in millimeters between the voxel and the nearest voxel in the bounding region. This expression for $C_a$ outside the bounding region is motivated by the idea that since the bounding region found at 606 in FIG. 6 may be inaccurate and cut off small parts of the organ, the segmentation mask should be allowed to grow a small distance outside the bounding region, but it should be increasingly difficult for the segmentation mask to grow far outside the bounding region. For subsequent iterations, $C_a$ is set to 5 for voxels with atlas probability of 0, or for voxels outside the bounding region, and $C_a$ is set to 3 for voxels with atlas probability between 0 and 0.5. It is potentially advantageous to give a higher atlas cost to voxels that have relatively low probability, or are outside the bounding region, in subsequent iterations, because the bounding region is likely to be more accurate in subsequent iterations, and thus the atlas probability is expected to more accurately reflect where the target organ might be located.

If it was decided, at 806, to use the intensity gradient in the cost, then the gradient cost $C_g$ depends on the intensity gradient magnitude of the voxel, defined in the same way as the intensity gradient magnitude was defined in 222 of FIG. 2, when finding the median and standard deviation of the intensity gradient magnitude in the training images, for internal and boundary voxels of the target organ. For example, the intensity gradient is optionally defined as the magnitude of the two-dimensional gradient in the axial slice of the voxel. If the magnitude of the gradient is less than the maximum normal inside gradient in the training data, defined as the median gradient for voxels inside the target organ, plus 1.5 times the standard deviation of the gradient for voxels inside the target organ, then $C_g$ is set to zero. If the magnitude of the gradient is greater than the maximum normal inside gradient, then $C_g$ is optionally given a positive value that depends linearly on the gradient for that voxel, for example going from 0 when the gradient is equal to the maximum normal inside gradient, to 20, or some other very high value, when the gradient is equal to the median gradient for boundary voxels in the training data. Making $C_g$ very high when the gradient is comparable to the median gradient for boundary voxels, has the potential advantage that it may tend to make the expansion reach the stopping condition when it reaches the boundary of the target organ, resulting in an accurate segmentation.

The volume cost $C_v$ differs from cost functions used in classical fast marching algorithms, because it is not a function only of the properties of the voxel, as the histogram, atlas, and gradient costs are, but it depends on the history of the expansion of the mask, because it depends on the volume of the mask so far, and because it depends on properties of distant voxels. Nevertheless, the inventors have found that using the volume cost often produces improved segmentation results, compared to not including the volume cost, and in particular it can help to prevent large leaks into neighboring organs that have similar intensity to the target organ. The volume cost $C_v$ optionally multiplies the other cost terms $C_h$, $C_a$, and $C_g$, in the formula used for the cost function. When the total volume of the mask is sufficiently small, for example less than the mean volume of the target organ minus the standard deviation of the volume of the target organ, in the training data, $C_v$ is optionally set to 1, so that the volume of the mask does not affect the cost. $C_v$ optionally rises slowly as the volume of mask increases from the mean volume minus the standard deviation of the volume, to the mean volume plus the standard deviation of the volume, and $C_v$ optionally rises more quickly as the volume of the mask increases above the mean volume plus the standard deviation of the volume. For example, $C_v$ is equal to 1 plus a function proportional to the square of the difference between the mask volume, and the mean volume minus the standard deviation of the volume in the training data, and $C_v$ reaches 8 when the mask volume is equal to the mean volume plus the standard deviation of the volume in the training data.

The cost function C for the voxel is optionally set equal to $C_v$ times $(C_h+C_a+C_g)$.

If the expansion is still near its beginning, for example if fewer than 8 voxels have been added to the segmentation mask so far, then the cost function is optionally never allowed to be greater than a maximum value, for example 10. This rule has been found to be potentially advantageous, because it may prevent the expansion from ending immediately after it starts, due to a noisy region around the seed, and it may ensure that a core region of the organ is entirely included in the mask, with voxels that have low path cost.

Morphological Fixing of Leaks

Figure 9:
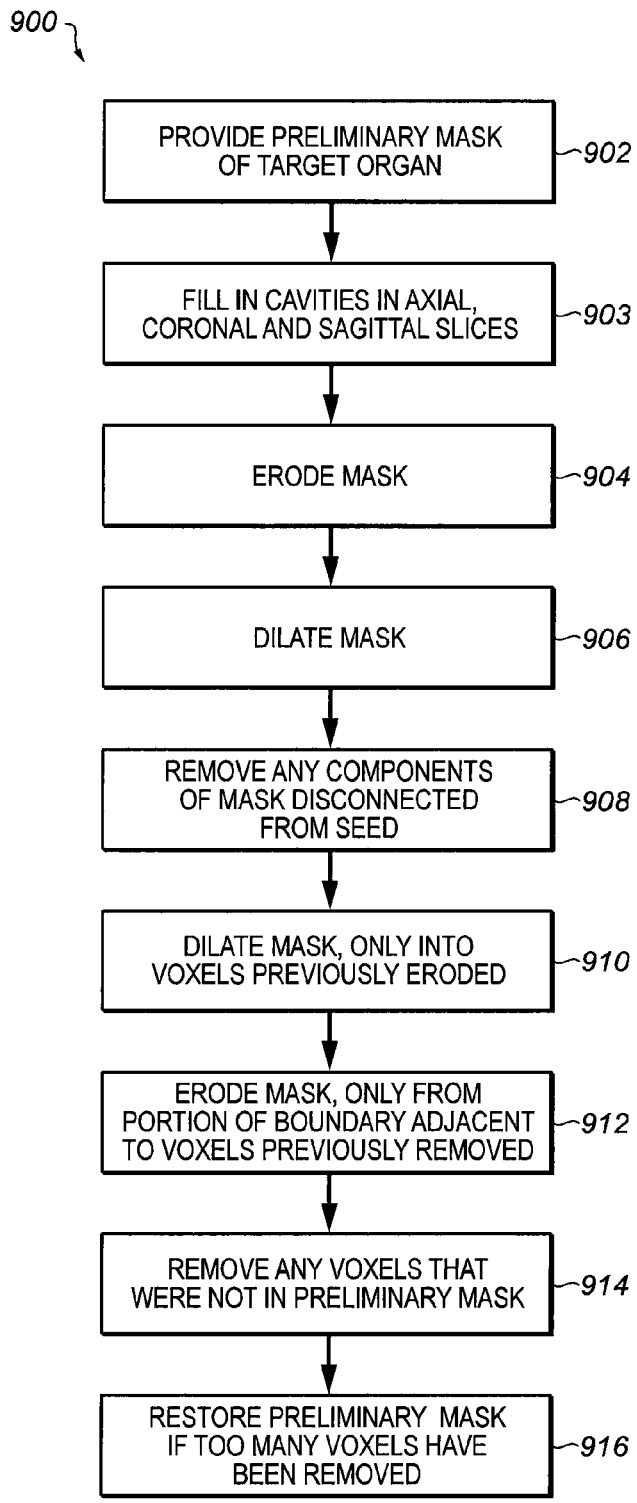
FIG. 9 is a flow chart showing further details of morphologically fixing leaks according to the method of FIG. 6.

FIG. 9 shows a flow chart 900, for a method of morphologically fixing leaks from one object into a neighboring object in an image, which may result from using a region-growing algorithm to segment the objects in the image. The method of flow chart 900 may be used, for example, to perform the morphological fixing of leaks from one organ into a neighboring organ or region, at 628 and 638 of FIG. 6. Although the method of flow chart 900 is described for the case where the objects are target organs in a medical image, it should be understood that the method can be used for other objects in other images as well. In general, the method is useful for objects that are expected to be reasonably convex, and not to have separate parts that are connected by a narrow neck, so if the segmentation does exhibit such a configuration, it can be assumed to be a result of a leak from one object into a neighboring object. It is known in image processing to correct such leaks by performing a large enough morphological opening to disconnect the two objects, and then to discard the part that is not wanted. However, in the prior art of performing morphological openings to fix leaks, the morphological opening also smoothes the boundaries on the rest of the mask, and the method of flow chart 900 has the potential advantage of restoring those boundaries to their original form, without restoring the leak.

Figure 10:
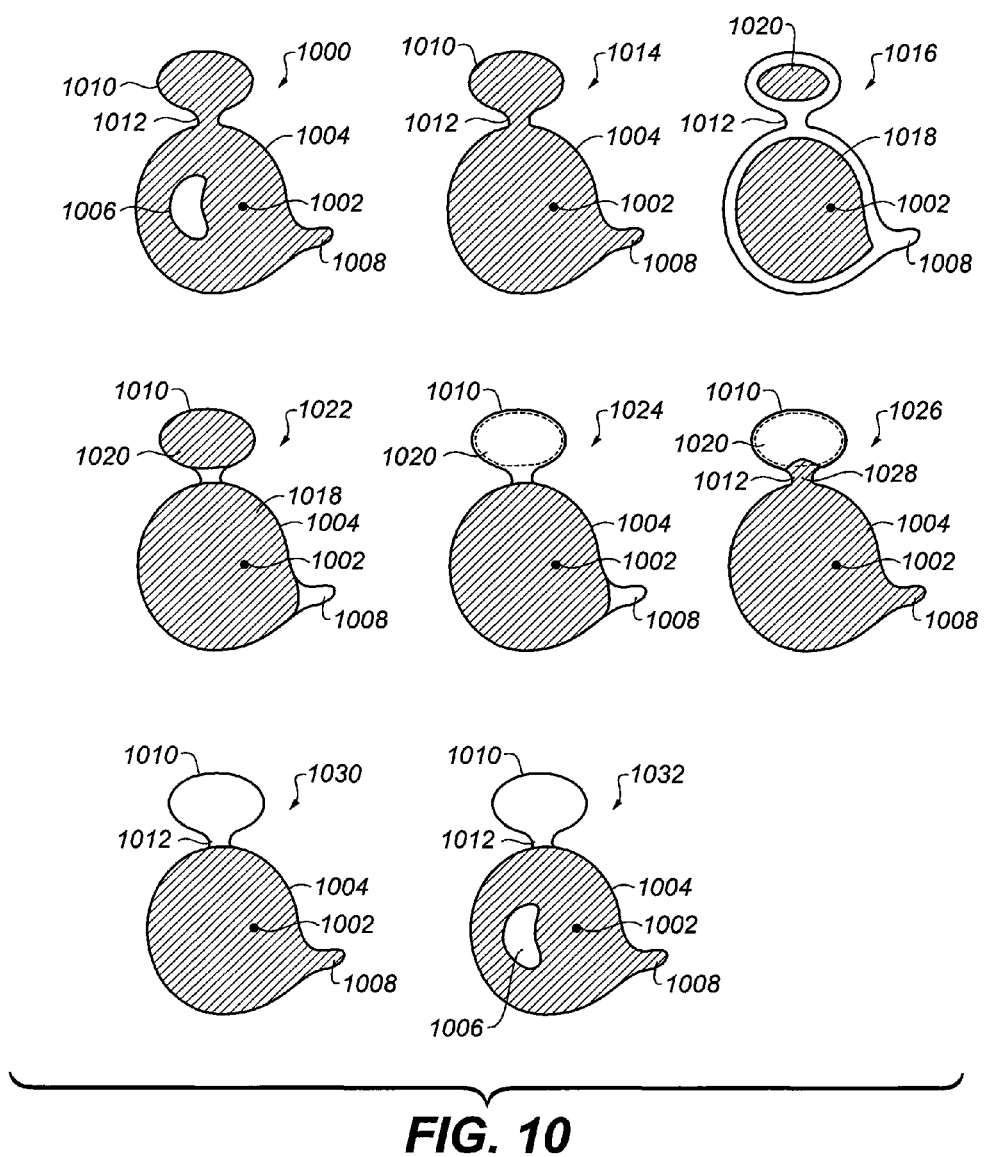
FIG. 10 is a schematic illustration of a two-dimensional cross-section of a segmentation mask of a target organ at different stages of the method of FIG. 9.

FIG. 10 illustrates the method of flow chart 900, by showing schematic views of two-dimensional cross-sections of an exemplary segmentation mask of a target organ, at different stages during the method of flow chart 900.

At 902, a mask is provided of a preliminary segmentation of the target organ, for example the output of the region-growing algorithm used at 624 in FIG. 6, and described in detail in FIG. 8A, with the addition of morphological filling done at 626 in FIG. 6. When the method of flow chart 900 is performed a second time, at 638 in FIG. 6, the preliminary segmentation has been further modified, by the procedures done at 634 and 636 to reassign overlap voxels to only one of the overlapping organs. The method of flow chart 900 is useful, in this context, when the seed is included in the mask of the preliminary segmentation, and this is always true when the method is performed the first time, at 628 in FIG. 6, because voxels have only been added to the mask, starting from the seed, in 624 and 626, and no voxels have been removed. When the method is performed the second time, at 638, some voxels may have been removed from the mask since it was grown from the seed, and in principle it is possible that the seed is no longer included in the segmentation. If this happens, then the method of flow chart 900 is optionally not performed at all, or the method of flow chart 900 is performed using a different criterion for removing components at 908, that does not depend on whether the component is connected to the seed. In practice, the inventors have found that this happens very rarely.

FIG. 10 shows a view 1000 of a cross-section of a segmentation mask as it would look before the method of flow chart 900 is performed. View 1000 includes a seed 1002, inside the mask. A main portion 1004 of the cross-section corresponds closely with the target organ in the plane of the cross-section, and has a completely surrounded cavity 1006, which is not part of the mask or the target organ, and a small projection 1008 which is part of the target organ. View 1000 also shows a leakage portion 1010 of the mask, which is part of a different organ, adjacent to the target organ and with similar intensity values to the target organ. The region-growing algorithm which produced the segmentation mask by mistake extended into leakage portion 1010, through a narrow neck 1012 where the two organs are touching or nearly touching. It is an object of the method of flow chart 900 to remove leakage portion 1010 from the segmentation mask, while preserving accurate boundaries for the target organ.

At 903, two-dimensional cavities in each axial, coronal or sagittal slice are optionally filled in. This is potentially advantageous particularly for the kidneys, to prevent the organ shape from being too thin and therefore easily deleted when a morphological opening is done at 904 and 906, since the kidneys have a hollow region near the center. FIG. 10 shows a view 1014 of the segmentation mask cross-section, after cavity 1006 has been filled in. It should be understood that, optionally, the filled-in cavities are later removed from the mask, at 914, so that filling in the cavities at 903 does not ultimately add them to the mask, but they are only added to the mask temporarily so that the morphological opening can be done at 904 and 906.

At 904 and 906, a large morphological opening is performed on the mask provided in 902, to disconnect leaks into adjacent structures. The morphological opening is done by eroding the mask at 904, which removes any narrow necks connecting the bulk of the mask from small leaks into adjacent organs, followed by dilating the mask, by the same number of voxels, at 906, which brings the boundary of the mask approximately back to its initial position in places where the boundary is fairly smooth and flat, but does not restore narrow necks, or other narrow projections, and regions that were disconnected by the erosion remain disconnected after the dilation, if they were only connected originally by a narrow neck.

View 1016 of FIG. 10 shows the mask cross-section after the mask has been eroded. The mask is now separated into a main portion 1018 which includes seed 1002, and leakage portion 1020, because narrow neck 1012 was eroded away. At view 1022, the mask has been dilated, and main portion 1018 of the eroded mask has expanded to fill up most of main portion 1004 of the original mask, and leakage portion 1020 of the eroded mask has expanded to fill up most of leakage portion 1010 of the original mask. But leakage portion 1020 is still separated from main portion 1018, and from seed 1002, because of the narrow neck that originally connected them. Also, main portion 1018 has not expanded enough to extend all the way into projection 1008, because it is so narrow. In view 1024, disconnected leakage portion 1020 has been removed from the mask. The mask now extends approximately back to its original boundaries in main portion 1004, and no longer extends into leakage portion 1010. However, in view 1024 the mask does not extend all the way into small projection 1008, even though projection 1008 is part of the target organ and should be included in the mask. The remaining elements of the method of flow chart 900 address this problem.

The opening distance, which is the distance of the erosion and of the dilation, is optionally proportional to $(3V/4\pi)^{1/3}$, where V is the volume of the mask. This would be the radius of the mask if it had a volume V and were spherical. The inventors have found that good results are obtained for the method of flow chart 900 if the proportionality constant is set to be 0.2 in the first iteration of the organ segmentation algorithm in FIG. 6, and 0.05 in subsequent iterations, if subsequent iterations are performed at 640 of FIG. 6. A possible reason why it may be advantageous to use a smaller morphological opening distance in subsequent iterations, than for the first iteration, is that in the first iteration, the atlas cost $C_a$ does not increase so much for voxels that have lower probability of being in the target organ according to probabilistic atlas, and the region-growing algorithm is fairly likely to leak significantly into adjacent organs or other structures with similar intensities, so it can be advantageous to erode a significant portion of the mask away, to leave only a core inner part of the mask, in order to best disconnect leaks into extraneous structures. In subsequent iterations, the atlas cost $C_a$ increases more rapidly for voxels that have a lower probability of being in the target organ, because the bounding region is considered more reliable, and hence the probabilities of the voxels being in the target organ, according to the probabilistic atlas, are considered more reliable. In this case, leaking of the region-growing algorithm into adjacent organs or other structures may be less likely, so it may not be advantageous to erode the mask by such a large distance.

At 908, after the morphological opening, optionally only the component of the mask (if any) that is connected to the seed is kept, and disconnected components are removed from the mask, as shown in view 1024 of FIG. 10. Alternatively, other criteria are used for deciding which component of the mask to keep. For example, only the component with the largest volume is kept, or only the component with intensity characteristics, for example a mean value of intensity or a distribution of intensities, that best matches the intensity characteristics expected for the target organ. Keeping only the component connected to the seed has the potential advantage that, assuming the seed is correctly located in the target organ, it can exclude components that are due to leaking into adjacent organs, even if they have very similar intensity characteristics to the target organ, and even if they are larger than the target organ. Optionally, components are removed from the mask only if they meet certain criteria, for example in volume and in intensity characteristics, and more than one component may be kept, or the procedure ends in failure if more than one component remains after removing components that meet the criteria for removal.

In some embodiments of the invention, components are removed at 908 before the eroded mask is dilated at 906. However, if the criterion for removing components at 908 is that they are not connected to the seed, then it is potentially advantageous to dilate the eroded mask at 906, before removing components at 908, because the seed may be removed from the mask in the erosion at 904 and restored to the mask in the dilation of 906. If the criterion for removing components at 908 does not depend on the component being connected to the seed, then there may be less reason to perform the dilation at 906 before removing components at 908.

At 910, the mask is dilated, but only into voxels that were eroded from the mask at 904. Optionally, the dilation is over the same distance as the erosion at 904 and the dilation at 906. The resulting mask is shown in view 1026 of FIG. 10. At this point, the boundary of the mask has returned to its original location, including in small projection 1008, except for regions that were originally connected to the main part of the mask by a narrow neck, and were removed at 908. In those regions, the mask now extends part way up the narrow neck, shown as region 1028 in view 1026 of FIG. 10 and another erosion step is performed at 912 to remove that part of the narrow neck from the mask. At 912, the mask is eroded, optionally by the same distance as the dilation at 910, but only from a portion of the boundary adjacent to voxels that were removed previously, at 904 or at 908. The resulting mask is shown in view 1030 of FIG. 10. This erosion step only affects the part of the mask that extended part way up the narrow neck at 910, region 1028 in FIG. 10, and serves to remove that part of the narrow neck from the mask. Thus, the procedure in 910 and 912 expands the segmentation back to its old boundaries in places where only a thin strip was removed, but keeps the new boundaries in places where a large component was disconnected.

At 914, any voxels that were not in the preliminary mask are optionally removed, optionally including the voxels that were added when filling in cavities at 903. The resulting mask is shown in view 1032 of FIG. 10, where the voxels in cavity 1006 have been removed because they were not part of the original mask. This can optionally be done at any time after the dilation of the mask at 906, since the procedures performed after 906 only remove voxels from the mask, and do not add voxels to the mask that were not in the mask before the erosion at 904.

At 916, a comparison is optionally made between the resulting new mask, and the preliminary mask provided at 902. If too much of the preliminary mask was deleted as result of steps 903 through 914, for example if more than 70% of the voxels in the preliminary mask were deleted, then optionally the mask is restored to be the same as the preliminary mask.

Reassigning Overlap Voxels

Figure 11:
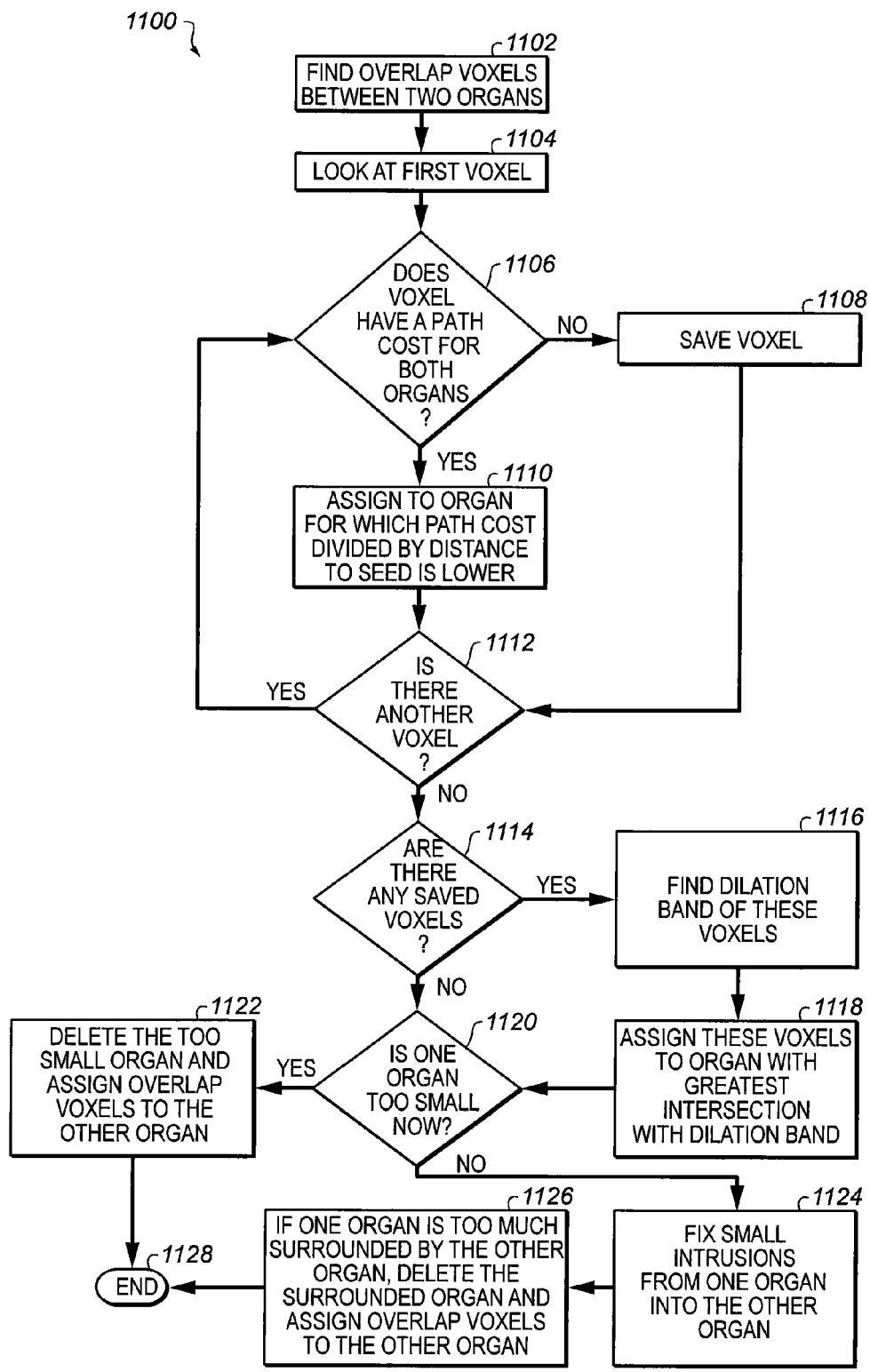
FIG. 11 is a flow chart showing further details of assigning overlap voxels to an organ, according to the method of FIG. 6.

FIG. 11 shows a flow chart 1100, for a method of assigning voxels, that fall in an overlap region between two target organs, to one of the target organs. In addition, when such an overlap region exists, the method includes some options of reassigning voxels to a different organ in certain cases where the voxels are not in the overlap region. The method of flow chart 1100 is used, for example, at 634 of FIG. 6.

Overlap between two segmented organs is likely to occur in two scenarios: (1) When two of the segmented organs share a boundary and have very similar intensities and very little gradient at their boundary. In such cases, often one or both segmentations will leak significantly over the boundary and into the adjacent organ. (2) When the seed for an organ segmentation was wrongly found in a different organ, usually near the boundary of the other organ closest to the target organ, so that much or all of one organ segmentation actually falls within the other organ; this scenario is relatively rare. In both cases, a goal of the method of flow chart 1100 is to reassign each voxel within the overlap region to only one of the two organs, and remove it from the other organ. In the second case, the organ whose seed was incorrectly placed cannot be correctly segmented, but the goal is to correctly assign all its overlap voxels to the other organ and to detect that this organ segmentation failed.

At 1102, a list of voxels in the overlap region, defined as voxels that are included in the masks for both organs, is found. At 1104, the first voxel is considered. At 1106, a determination is made as to whether the voxel being considered has a path cost associated with it, for both of the two overlapping target organs. If the voxel was added to the segmentation mask for one of the organs while performing the region-growing algorithm at 624, then there will be a path cost associated with the voxel for that organ, the integrated cost over the path of expansion from the seed of that organ to that voxel, for example as found at 816 in FIG. 8. But if the voxel is part of the seed for one of the organs, or if the voxel was added to the segmentation mask as part of a morphological filling or fixing at 626 or 628 of FIG. 6, then there will be no path cost associated with the voxel, for that organ. If the voxel does not have a path cost for at least one of the overlapping organs, then the voxel is saved, at 1108, to be examined later. If the voxel does have a path cost for both of the organs, then, at 1110, a comparison is made between quantities that are characteristic of an average of the cost function over the path of expansion for each organ, and the voxel is assigned to the organ for which the quantity is lower, and removed from the other organ. For example, the comparison is made between the path cost of the voxel divided by the Euclidean distance from the voxel to the seed, for each organ, and the voxel is assigned to the organ for which the path cost divided by Euclidean distance to the seed is lower. Alternatively, the comparison is made between the actual average of cost function for all the voxels on a path of lowest path cost leading to the voxel being considered, and every time a new path cost is calculated when running the region-growing algorithm, a corresponding average cost function is also calculated and associated with that voxel, or an algorithm such as gradient descent is used to find the set of voxels that lies along an optimal path from the voxels back to the seed, and the average cost function of these voxels is found. But using the path cost divided by Euclidean distance has the potential advantage that it is not necessary to keep track of the average cost function when running the region-growing algorithm. Comparing a quantity that is characteristic of average cost function over the path of expansion, rather than comparing path cost directly, has the potential advantage that the procedure will not give preference to the smaller organ, which is likely to have a shorter expansion path to the voxel simply because its boundary voxels lie closer to its seed due to its small size, and may have a smaller path cost for that reason alone.

A determination is made at 1112, as to whether there remain any more voxels to examine. If there are more voxels, then the next voxel is examined at 1106, to determine whether it has a path cost associated with both organs. If there are no more voxels to examine, then at 1114, a determination is made as to whether there are any voxels that were saved at 1108, not yet assigned to one of the organs, because they did not have a path cost for both organs.

If there are any saved voxels, then a dilation band for the saved voxels is found at 1116. The dilation band is found by dilating the set of saved voxels, a distance of one voxel, and then removing the saved voxels from the resulting set of voxels. At 1118, the saved voxels are assigned to the organ with the greatest intersection with the dilation band, and removed from the other organ. Roughly speaking, the saved voxels are assigned to the organ that most fully surrounds them. The saved voxels, since they were added to at least one of the organs by morphological operations, are generally largely surrounded by voxels that were initially in that organ, maybe in both organs, and those voxels are usually assigned to one of the organs at 1110, so typically, if there is only one component of saved voxels, it will be largely surrounded by voxels assigned to its correct organ. There may be two or more component of saved voxels, some of them surrounded by voxels assigned to one of the organs at 1110, and some of them surrounded by voxels assigned to the other organ, and according to the procedure of 1118, all of them will now be assigned to the organ surrounding the component with the bigger surface area. However, in that case, the incorrectly assigned saved voxels will likely be correctly assigned to the other organ later, at 1124.

At 1120, a determination is made whether one of the organs is too small now, compared to the size expected for that organ from the training data. For example, an organ is considered too small if its volume is less than the mean volume for that organ in the training data, minus 3 times the standard deviation of the volume for that organ, as found at 224 in FIG. 2. If one of the organs is too small, after reassigning its overlap voxels to the other organ, then it is likely that by mistake, it was grown from a seed that is really located in the other organ. In that case, at 1122, all of the overlap voxels of the too small organ are assigned to the other organ, and the too small organ is deleted. In this circumstance, no further attempt is made to segment the deleted organ, and the procedure ends at 1128. The inventors have found that this often happens because the deleted organ has been surgically removed from the patient, or is missing for some other reason, making it impossible to segment it.

Otherwise, at 1124, small intrusions of one of the organs into the other organ are fixed. Such intrusions may be caused, for example, by noise in the image which affects the path costs, or by the practice, in 1118, of assigning all saved voxels to the organ that has the greatest intersection with the dilation band, even though there may be two components of such voxels, some of them belonging to one organ and some of them belonging to the other organ. The inventors have found that the following method for fixing small intrusions works well: 1) First find voxels that are located in any two-dimensional cavity in any axial, sagittal or coronal slice, for each of the two organs. If any of these voxels were originally overlap voxels, then assign them now to the organ that is surrounding the cavity, rather than to the other organ. 2) Next, perform a morphological opening (erosion followed by a dilation of the same number of voxels) on the segmentation mask for each of the two organs, by a small number of voxels, for example by 2 voxels, and reassign any overlap voxels that were deleted from one organ by this opening to the other organ instead. 3) Any voxels that are not overlap voxels, that were deleted from one organ by this morphological opening, and are very close to the other organ, for example within 2 voxels of the other organ, remain deleted from the first organ, but are not assigned to the other organ. 4) Any other voxels that are not overlap voxels, that were deleted from one organ, are assigned again to the organ they were deleted from.

At 1126, a determination is made whether one of the two organs is too much surrounded by the other organ. This is done, for example, by creating a mask of the dilation band of one organ, and seeing whether too large a percentage of the dilation band voxels, for example more than 35% of the dilation band voxels, sit within the other organ. In this case, it is likely that the surrounded organ was grown from a seed that was located by mistake inside the other organ, possibly because the surrounded organ is missing from the patient, and all of the original overlap voxels of the surrounded organ are then assigned to the other organ, and the surrounded organ is deleted. No further attempt is made to segment the deleted organ, and the procedure ends at 1128.

If the method of flow chart 1100 is being done as part of 634 in FIG. 6, then the method is repeated for any other pairs of organs for which there are overlap voxels. Optionally, the procedure of 636, removing small regions that have become disconnected from the seed of the organ as a result of reassigning overlap voxels, is done immediately after the method of flow chart 1100 is completed for each pair of overlapping organs, instead of waiting until overlap voxels have been reassigned for all organs.

Fully Automated Segmentation System

Figure 12:
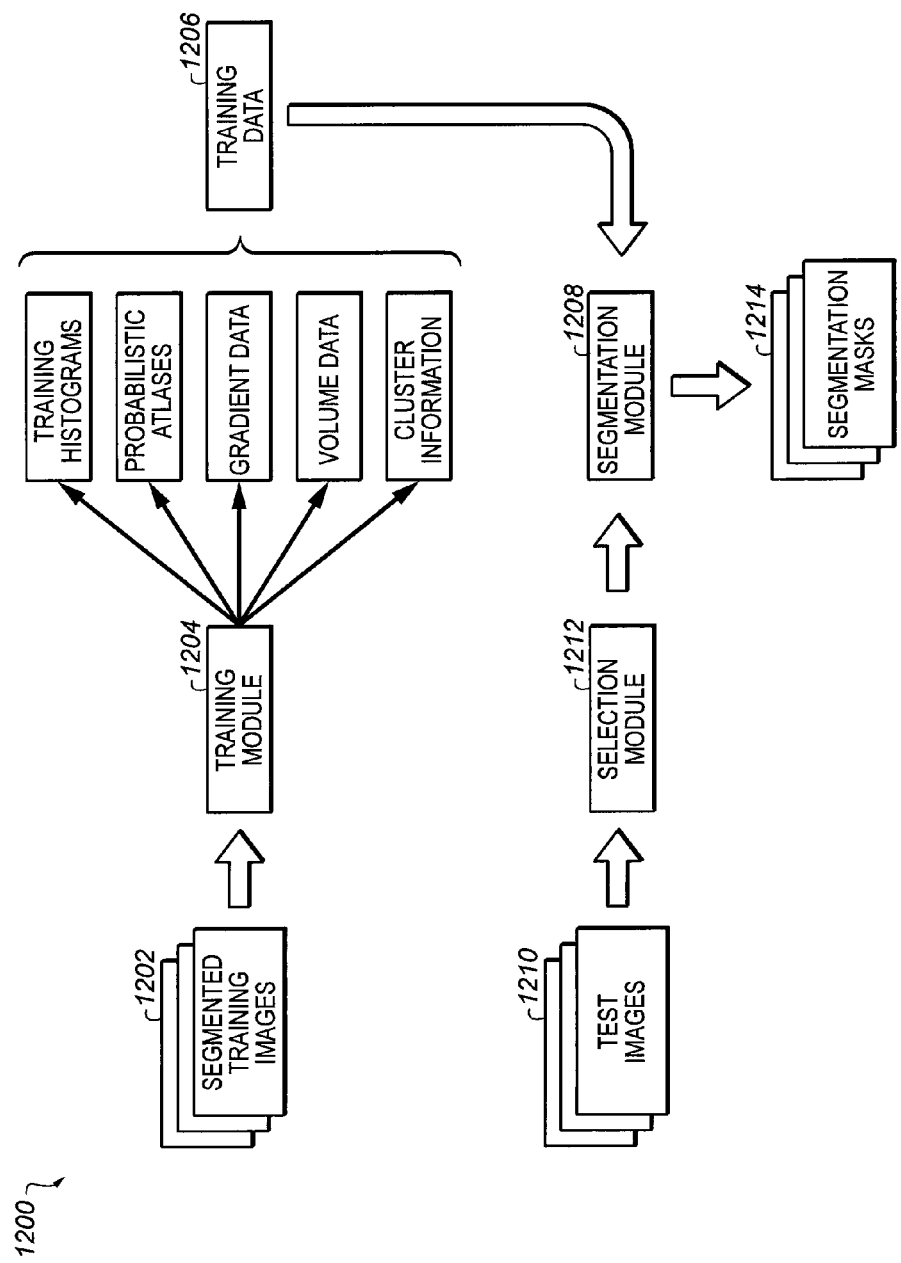
FIG. 12 is a block diagram showing a system for performing the method of FIG. 1, according to an exemplary embodiment of the invention.

FIG. 12 shows a block diagram for a system 1200, in the form of a data processor or computing device, using the approach outlined in FIG. 1, that can fully automatically segment a plurality of different target organs appearing in a database of medical images. A set 1202 of already segmented training images, showing the target organs, is used as input for a training module 1204. Images 1202 are in digital format, stored on a digital data storage device, such as a hard drive. The training module is, for example, a set of software instructions that a general purpose computer, or any other data processor or computing device, is programmed or otherwise configured to run, that produces training data 1206 as output using the training images, for example using the method shown in FIG. 2. The training data optionally includes one or more of training histograms, probabilistic atlases, gradient data, and volume data, for each target organ, stored on a digital data storage device, such as a hard drive, possibly incorporated into a software program supplied to an end user, for example on an optical disk, or on a server available for downloading. If clustering is used to group images with different contrast characteristics, then the training histograms and gradient data are optionally produced for each cluster for each target organ, and an average or representative intensity data, such as an average or representative intensity histogram, is optionally found and included in the training data for each cluster for each target organ, optionally for the entire bounding region of the target organ, so that test images can be assigned to a cluster. The training data is incorporated into a segmentation module 1208, which can be run on a general purpose computer or any other computing device, programmed or otherwise configured to segment the target organs in test images, using the training data. For example, segmentation module 1208 segments test images using the method shown in FIG. 6. Test images 1210 are used as input for segmentation module 1208. Test images 1210 are in a digital format, stored on a digital data storage device such as a hard drive. Optionally, a selection module 1212 automatically selects test images which include the target organs, or are expected to include the target organs. For example, if the target organs are in the abdomen, then the selection module selects test images with a field of view that includes the entire abdomen, or that includes all of the part of the abdomen where the target organs are located, or that is expected to include at least parts of the target organs. An example of a method that can be used to select such images is described in U.S. Pat. No. 8,170,306 to Yu et al, or any other method known in the art is optionally used. Segmentation module 1208 uses training data 1206 to segment test images 1210, at least the ones selected by selection module 1212, and outputs the result as segmentation masks 1214. Segmentation masks 1214 are optionally displayed to a user on a graphic display device, for example overlayed on the test images, and/or are stored on a digital storage device for later use. Alternatively, the segmentation results are used directly by an application, such as an automated statistical analysis of images acquired at a particular facility, that does not require ever displaying segmented images to a user. Some applications for such automatically segmented images are described below.

Although the same computer is optionally used both for training module 1204 and segmentation module 1208, often different computers are used, because the training data is optionally produced once, in order to incorporate it into a segmentation program that can be used by the segmentation module, and the segmentation program may then be sold as a stand alone software product, which can be used by an end user to segment test images on any computer.

The approach to automatic segmentation of organs, embodied in FIG. 1 and in FIG. 12, has several advantages:

The method is generic for many types of organs, and a new, unseen organ class may be added without making any changes to the code, simply by adding training examples of this organ. The inventors tested the generic nature of the algorithm by initially working only on the spleen, left kidney, and right kidney, and then adding in the liver without changing the code. Equally good results were obtained on the liver, with no need to modify the algorithm, as on the organs used during algorithm development. Some data on these results is provided below, in the "Examples" section.

The method works well for images with widely variant fields of view, resolutions, contrast agent usage, noise levels, anomalies and pathologies, and other characteristics, as long as the training set is broad enough to encompass the desired range. Furthermore, the training set can always be broadened to better represent any class of test images that is found not to be segmented well.

The method for segmenting test images is very fast, on the order of a few seconds on a quad-core Intel Xeon 3.4 GHz computer, to segment four large abdominal organs, the liver, spleen, left kidney, and right kidney, including the preprocessing to predict organ bounding regions. It could be sped up even further with more careful optimization.

The method for segmenting test images is fully automatic, requiring no user input, guidance, or interaction whatsoever, including automatically deciding the field of view of an unseen test image and assessing its relevance, so that the algorithm is run only on test images that include the target anatomy. It is therefore possible to run the algorithm as soon as the test image is saved after the patient is scanned, even before a radiologist loads the image to do reading and reporting, so that the algorithm will run off-line and take up zero time from the user's point of view.

Applications of the Automatic Segmentation Method

The capability of the method of FIG. 1 to reliably and quickly segment organs in medical images with no human intervention makes it useful for a number of different applications:

Automatically detecting the organs included within an unseen scan, for use in automatically creating a searchable database of imaging studies containing various organs, or for use in gathering statistics of studies for a given hospital, or for use in gathering statistics on a given organ from a large body of organ segmentations.

Using the generated organ segmentation to allow automatic and optimal navigation such as panning, zooming, and/or windowing for each detected organ, based on its automatically-detected location, extent, and grayscale values.

Automatically finding all references in the radiology report to detected organs, optionally making use of natural language processing, and automatically turning the corresponding words in the report into hyperlinks, such that, when pressed, they navigate the user directly to the relevant organ, optionally also adjusting the zoom and/or windowing to optimize it for the current organ.

Creating a "per-organ windowing" display module so that, for example, when viewing any slice of a three-dimensional image, the user sees all voxels belonging to the liver with optimal or standard liver windowing parameters, all voxels belonging to the lungs with optimal or standard lung windowing parameters, etc. An example of such a "per-organ windowing" module is described, for example, in a provisional U.S. patent application with Ser. No. 61/974,077, titled "Organ-Specific Image Display", filed on Feb. 4, 2014. Optionally, the per-organ windowing parameters are selected differently for each cluster of images with similar contrast characteristics, if such clusters are used, to enable different windowing values depending on the presence of contrast agent. Optionally, if dual-energy CT scans are available, they are used to produce an optimal bone mask and to give those voxels bone windowing, by using the fact that a given bone voxel will differ in intensity, at the two x-ray energies, more than a non-bone voxel. Optionally, for example in scans without dual energy, a bone segmentation algorithm, such as any available in the literature, may be used to produce a bone mask for bone windowing.

Automatically computing the volume of each detected organ and optionally including the volumes in the report, and optionally triggering a warning when detecting an organ volume that is unusually large or small, to draw the radiologist's attention to a possible pathology.

Automatically dividing scans with a larger field of view into individual groups representing the chest, abdomen, and/or pelvis, a procedure which is currently carried out manually at many sites.

Upon loading an imaging study of a patient for whom there exist studies done at other times which the radiologist might wish to compare, using the body parts present in each group to automatically decide which groups to register with which, instead of waiting for user input as to which groups should be registered together.

Using each whole-organ segmentation as a starting point for more detailed segmentation of this organ, for example segmenting the lobes of the liver and lungs, segmenting the heart atriums and ventricles, segmenting the major blood vessels of each organ, and/or automatically finding lesions in each organ.

Automatically detecting the organ or other body part in which a user marking (for example, a user-generated graphic or a pathology segmentation) lies. This detection makes it possible to correctly label the user marking as belonging to the enclosing organ, for example in the radiology report. For example, if the radiologist draws a line within a liver lesion to measure its longest diameter, it is possible to automatically add to the report that this lesion is a liver lesion. After detecting the body part that each user marking falls in, a map or sketch of the human body is optionally drawn, highlighting the parts in which findings exist, optionally allowing navigation to the relevant findings by clicking on them in this map.

For this last application, lesions that lie on the boundary of an organ, but are excluded from its segmentation because they have very different intensity properties than the organ itself, can still be correctly detected as follows: After the end of the method of flow chart 600 in FIG. 6, when all of the target organs have been segmented, the segmentation mask of each organ is dilated by a short distance, for example 5 mm, but only into voxels that do not already belong to the mask of another organ. This dilation will add to the mask of each organ at least some of the voxels that belong to any lesions lying along the boundary of that organ thereby assuring that the mask overlaps the lesion. Optionally, the dilation only includes voxels with intensity values that are possible for such lesions, but excludes, for example, intensity values typical of the abdominal cavity, or intensity values typical of dense bones. However, including voxels that belong to the abdominal cavity will not matter very much, as long as voxels are not included in the dilation that belong to adjacent organs, on which a user marking might be placed. Then, if a user marking, and/or an automatic or semi-automatic lesion segmentation, sufficiently overlaps the dilated mask of an organ, because it is marking a lesion on the surface of the organ, it is optionally automatically labeled as belonging to that organ.

Although the description herein generally refers to detecting or segmenting organs, it should be understood that the methods described herein can also be used for detecting or segmenting any structures or objects in a medical image, such as lesions within an organ, or components of organs, or cavities or lumens inside hollow organs, or bones, or skeletal muscles. In some of these cases, the method may work better if it is modified. Some useful modifications, for the case of segmenting lesions on the surface of an organ, have already been described above.

For segmenting bones, and skeletal muscles, the bounding region is optionally not required to be aligned with the principle axes of the body, but is aligned with the expected axis of the bone, which for some bones may be very different from the principle axes of the body. Particularly for long bones of the limbs and their associated muscles, the orientation of the bone may vary greatly between images, and the orientation of the bone in the image is optionally determined or estimated from the test image, based for example on the high density portion of the bone, before the bounding region is found.

In the case of long thin lumens such as blood vessels, again the bounding region is optionally aligned with the expected axis of the blood vessel or lumen, rather than with the principle axes of the body, and in the case of blood vessels in the limbs, their orientation is optionally inferred from the orientation of corresponding bones in the limbs.

Lumens which do not rigidly hold their shape, such as the lumens of the gastrointestinal tract, are optionally imaged when they are filled with a fluid, for example a fluid containing a contrast material such as barium in the case of CT images of the gastrointestinal tract, which will make their shape and internal intensity more predictable, and will make the lumen more visible.

For segmenting components of organs, such as lobes of the lungs or the liver, heart valves and heart chambers, and blood vessels that belong to organs, the organ is optionally segmented first, and bounding box of the component of the organ is optionally found relative to the bounding box of the organ, or relative to a salient feature of the organ.

It is expected that during the life of a patent maturing from this application many relevant imaging modalities and region-growing algorithms will be developed and the scope of the terms "image" and "region-growing algorithm" are intended to include all such new technologies a priori.

As used herein, the term "providing" an item, for example a probabilistic atlas, includes obtaining that item in any way, including generating the item, or importing the item when it was previously generated by someone else.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

A fully automated segmentation system, as described above, was tested using 100 CT images of the abdomen that were acquired by various hospitals for a wide variety of purposes from a variety of patients, with a range of different imaging parameters such as field of view, resolution, x-ray energy, and contrast agent use. The spleen, left kidney, right kidney, and liver were used as target organs, and were manually segmented in all 100 images. Some of the images, for example 80 images, were then selected at random to be training images, and the other images were used as test images, to test the automated segmentation system against the manual segmentation, which was considered to be the true segmentation. For each of the test images, for each target organ, the coverage and the specificity were found. The coverage is defined here as the fraction of the volume of the true segmentation that was included in the segmentation mask found by the automated segmentation system. The specificity is defined here as the fraction of the volume of the segmentation mask found by the automated segmentation system, that belongs to the true segmentation.

This test produced the following results, for median coverage and median specificity for each target organ, for the 20 test images:

| Target Organ | Median coverage | Median specificity |
| --- | --- | --- |
| Spleen | 95% | 100% |
| Left kidney | 94% | 100% |
| Right kidney | 95% | 99% |
| Liver | 95% | 99% |

The parameters used for the training and for segmentation were chosen to produce good results for the spleen, left kidney and right kidney, but without doing any tests to see how well the program performed for the liver. The completed program, with its parameters fixed, was then tested with the liver as a target organ, as well as with the spleen, left kidney, and right kidney. The fact that the median coverage and median specificity were about as high with the liver as they were with the other target organs suggests that the program will work well for other target organs as well, as long as training is done with those organs, without any need to further adjust the parameters of the program.

Applicants have described a method of segmenting an organ in a medical image, comprising: identifying one or more seed voxels as being within the organ in the medical image; and using a region-growing algorithm to generate a segmentation mask of the organ from the one or more seed voxels, by running the region-growing algorithm on a data processor, wherein the region-growing algorithm uses a cost function for voxels that depends both on one or more local voxel characteristics, and on a total volume reached so far in the region-growing, the cost function being higher for the total volume greater than a greatest complete volume expected for the organ than for the total volume less than a smallest complete volume expected for the organ.

This method can further comprise displaying, storing or transmitting the generated segmentation mask, or information obtained from the generated segmentation mask.

Applicants have described a system for segmenting an organ in a medical test image, comprising: an input device that receives a digital medical test image showing the organ; and a data processor with access to the test image, programmed to generate a segmentation mask of the organ in the test image, using a region-growing algorithm with a cost function that depends both on one or more local voxel characteristics, and on a total volume reached so far in the region-growing, the cost function being higher for the total volume greater than a greatest complete volume expected for the organ than for the total volume less than a smallest complete volume expected for the organ.

Applicants have described a method of segmenting a target object in a medical image, with no or reduced leaking into other adjacent objects in the image, comprising: a) providing a mask of the target object in the image; b) eroding the mask a first time by a number n of voxels; c) dilating the mask a first time, by n voxels, after eroding the mask the first time; d) removing from the mask one or more components of voxels of suspected leaking, the component(s) satisfying one or more removal criteria, after eroding the mask the first time, and either before or after dilating the mask the first time; e) dilating the mask a second time by a number m of voxels, only into voxels that were eroded in (b), after removing the one or more components of voxels of suspected leaking, and after dilating the mask the first time; f) eroding the mask a second time, by m voxels, after dilating the mask the second time, only from a portion of the mask's surface that is adjacent to voxels that were in the mask as provided in (a), but have since been removed or eroded; and g) removing from the mask voxels, if there are any, that were not present in the mask as provided in (a), at any time after dilating the mask the first time.

This method can further comprise displaying, storing or transmitting the mask, or information obtained from the mask, after performing (a) through (g).

This method can further comprise providing a mask of the target object comprises identifying one or more seed voxels as being within the target object in the image, and using a region-growing algorithm to grow the mask from the one or more seed voxels. In addition, the removal criterion is disconnected in the mask from all of the one or more seed voxels.

Applicants have described system for segmenting a target object in a medical test image, comprising: a) an input device that receives a digital medical test image showing the organ; and b) a data processor with access to the test image, programmed to segment the organ in the test image by: i) providing a mask of the target object in the image; ii) eroding the mask a first time by a number n of voxels; iii) dilating the mask a first time, by n voxels, after eroding the preliminary mask; iv) removing from the mask one or more components of voxels of suspected leaking, the component(s) satisfying one or more removal criteria, after eroding the mask the first time, and either before or after dilating the mask the first time; v) dilating the mask a second time by a number m of voxels, only into voxels that were eroded in (ii), after removing the one or more components of voxels of suspected leaking, and after dilating the mask the first time; vi) eroding the mask a second time, by m voxels, after dilating the mask the second time, only from a portion of the mask's surface that is adjacent to voxels that were in the mask as provided in (a), but have since been removed or eroded; and vii) removing from the mask voxels, if there are any, that were not present in the mask as provided in (a), at any time after dilating the mask the first time.

Applicants have described a method of segmenting a plurality of target objects in a medical image, comprising: a) identifying one or more seed voxels for each of the target objects; b) generating a binary segmentation mask of each of the target objects from that object's one or more seed voxels, at least using a region-growing algorithm, wherein growing the masks of different target objects is done independently, without regard to whether or not there is any overlap between the masks of the different target objects; c) identifying a non-empty overlap region of the masks of a set comprising at least some of the target objects; and d) generating a revised mask of each of one or more of the target objects by assigning each of at least some voxels in the overlap region to only one of the target objects in the set.

The method can further comprise displaying, storing or transmitting the revised mask, or information obtained from the revised mask, of one or more of the target objects.

The method can further comprise assigning a voxel in the overlap region to one of the target objects comprises, for voxels that were added to the mask by the region-growing algorithm: determining a measure of average cost function along a path taken by the region-growing algorithm from one of the one or more seed voxels to the voxel being assigned, for each target object in the set; and assigning the voxel to the target object for which the measure of average cost function is lowest.

The method can further comprise assigning at least some voxels in the overlap region to one of the target objects comprises: determining the target object in the set for which the mask of the target object most fully surrounds the overlap region; and assigning at least a portion of the voxels in the overlap region to the target object for which the mask most fully surrounds the overlap region.

The method can further comprise assigning at least some voxels in the overlap region to one of the target objects comprises: comparing the volume of the mask of each target object in the set to an expected volume for that target object; and if the volume of the mask is sufficiently smaller than an expected volume of the target object for all but one of the target objects in the set, then assigning all of the voxels of the overlap region to that target object.

Applicants have described a system for segmenting a plurality of target objects in a medical test image, comprising: a) an input device that receives a digital medical test image showing the organ; and b) a data processor with access to the test image, programmed to segment the organ in the test image, by: i) identifying one or more seed voxels for each of the target objects; ii) generating a binary segmentation mask of each of the target objects from that object's one or more seed voxels, at least using a region-growing algorithm, wherein generating the masks of different target objects is done independently, without regard to whether or not there is any overlap between the masks of the different target objects; iii) identifying a non-empty overlap region of the masks of a set comprising at least some of the target objects; and iv) assigning each of at least some voxels in the overlap region to only one of the target objects in the set.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of segmenting a target organ of the body in medical images, the method comprising:
   a) providing a probabilistic atlas with probabilities for a presence of the target organ at different locations relative to a bounding region of the target organ;
   b) providing one or more medical test images;
   c) for each of the one or more medical test images, identifying, at least provisionally, a location of a bounding region for the target organ in the test image; and
   d) for each of the one or more medical test images, generating a segmentation mask of the target organ in the test image using the probabilities from the probabilistic atlas, wherein generating the segmentation mask is performed by a data processor, and wherein generating the segmentation mask of the target organ comprises finding a core region of voxels that have locations within the bounding region where the target organ is considered likely to be located according to the probabilistic atlas, and most of which have intensity values expected for the target organ.

2. The method according to claim 1, further comprising displaying, storing, or transmitting the generated segmentation mask, or information obtained from the generated segmentation mask.

3. The method according to claim 1, further comprising generating the probabilistic atlas independently of the test image.

4. The method according to claim 3, wherein generating the probabilistic atlas is accomplished before providing the test image.

5. The method according to claim 3, further comprising selecting a set of training images of the target organ to use in generating the probabilistic atlas, wherein generating the probabilistic atlas is done using all of the selected training images.

6. The method according to claim 5, wherein selecting the set of training images is done before providing the test image.

7. The method according to claim 1, wherein the probabilistic atlas has a gradient in probability as a function of location, that is greatest within one voxel of a location corresponding to a boundary of the bounding region.

8. The method according to claim 1, wherein the probabilistic atlas has a gradient in probability as a function of location, that is greatest at a location where the probability is less than 0.2.

9. The method according to claim 1, wherein at least 15% of the voxels in the atlas corresponding to locations in the bounding region have probability between 20% and 80%.

10. The method according to claim 1, wherein the bounding region can be completely parameterized by upper and lower bounds in each of three principal body directions, and using the probabilities from the probabilistic atlas to generate the segmentation mask of the target organ comprises:
    registering the bounding region of the target organ identified in the test image to the probabilistic atlas, by matching the upper and lower bounds in each of the three body directions to upper and lower bounds of the probabilistic atlas in each of the three body directions; and
    using the probabilistic atlas to find a probability for each voxel in the bounding region in the test image to belong to the target organ, according to the registration.

11. The method according to claim 1, wherein using the probabilities from the probabilistic atlas to generate the segmentation mask of the target organ comprises:
    determining a weighting factor for each voxel in the bounding region identified in the test image, based on the probabilistic atlas;
    calculating information on a weighted distribution of intensities, for the voxels in the bounding region of the test image, each voxel weighted by the weighting factor; and
    using the information on the weighted distribution of intensities to generate the segmentation mask of the target organ.

12. The method according to claim 11, wherein using the information on the weighted distribution of intensities comprises finding a core region of voxels that have locations within the bounding region where the target organ is likely to be located according to the probabilistic atlas, and most of which have intensity values expected for the target organ according to the information on the weighted distribution of intensities.

13. The method according to claim 1, wherein using the probabilities of the probabilistic atlas to generate the segmentation mask of the target organ in the test image comprises:
    using the probabilistic atlas to determine one or more voxels in the test image that are considered likely to belong to the target organ; and
    using a region-growing algorithm to generate the segmentation mask of the target organ starting from the one or more voxels as seed voxels.

14. The method according to claim 1, wherein using the probabilities of the probabilistic atlas to generate the segmentation mask of the target organ in the test image comprises using a region-growing algorithm to generate the segmentation mask of the target organ starting from one or more seed voxels, the region-growing algorithm using a cost function that depends on probability values of voxels being located in the target organ according to the probabilistic atlas.

15. The method according to claim 14, wherein using the probabilities of the probabilistic atlas to generate the segmentation mask of the target organ further comprises finding a core region of voxels that have locations within the bounding region where the target organ is likely to be located according to the probabilistic atlas, and most of which have intensity values expected for the target organ, and wherein the one or more seed voxels are located in the core region, and the region-growing algorithm is programmed to stop the growing at any voxel for which a path cost exceeds a threshold cost, and the cost function of most voxels in the core region is sufficiently low so that the path cost of most voxels in the core region is less than 20% of the threshold cost.

16. The method according to claim 1, further comprising:
using the segmentation mask of the target organ to find a second estimate of a location of the bounding region in the image; and
using the probabilistic atlas and the second estimate of the location of the bounding region to find a second segmentation mask of the target organ.

17. A system for segmenting a target organ in a medical image, the system comprising:
a) an input device that receives a digital test image;
b) a data storage device that stores a probabilistic atlas with probabilities for the presence of the target organ at different locations relative to a bounding region of the target organ; and
c) a data processor with access to the test image and the probabilistic atlas, programmed to:
   i) identify, at least provisionally, a location for a bounding region of the target organ in the test image; and
   ii) use the probabilities in the probabilistic atlas to segment the target organ in the test image, by finding a core region of voxels that have locations within the bounding region where the target organ is considered likely to be located according to the probabilistic atlas, and most of which have intensity values expected for the target organ.

18. The system according to claim 17, wherein the data processor is programmed to use the probabilities in the probabilistic atlas to find a seed voxel in the bounding region of the test image that is likely to belong to the target organ, and to use a region-growing algorithm to grow a segmentation mask of the target organ from the seed voxel.

19. The system according to claim 18, wherein the data processor is programmed to use a cost function based at least in part on the probabilities in the probabilistic atlas to grow the segmentation mask of the target organ from the seed voxel.

* * * * *